(12) United States Patent
Rameshwar

(10) Patent No.: US 7,119,071 B2
(45) Date of Patent: Oct. 10, 2006

(54) AMINO TERMINAL SUBSTANCE P COMPOSITIONS AND METHODS FOR USING THE SAME

(75) Inventor: Pranela Rameshwar, Maplewood, NJ (US)

(73) Assignee: University of Medicine and Dentistry of New Jersey, New Brunswick, NJ (US)

( * ) Notice: Subject to any disclaimer, the term of this patent is extended or adjusted under 35 U.S.C. 154(b) by 207 days.

(21) Appl. No.: 10/154,332

(22) Filed: May 21, 2002

(65) Prior Publication Data

US 2003/0225010 A1    Dec. 4, 2003

(51) Int. Cl.
*A61K 38/07*    (2006.01)
*C07K 5/10*    (2006.01)

(52) U.S. Cl. .......................... 514/18; 530/330
(58) Field of Classification Search .............. 514/2; 530/300
See application file for complete search history.

(56) References Cited

U.S. PATENT DOCUMENTS 5,891,842 A * 4/1999 Kream ................ 514/2

OTHER PUBLICATIONS

P Rameshwar and P Gascon. Induction of negative hematopoietic regulators by neurokinin-A in bone marrow stroma. (1996) Blood, 88, 98-106.*
DM Katschinski, et al. Whole body hyperthermia cytokine induction: a review, and unifying hypothesis for myeloprotection in the setting of cytotoxic therapy. (1999) Cytokine and Growth Factor Reviews 10, 93-97.*
MPN Nair and SA Schwartz. Substance P induces tumor necrosis factor in an ex vivo model system. (1995) Cellular Immunology, 166, 286-290.*
J Rudinger. Characteristics of the amino acids as coponents of a peptide hormone sequence. (1976) In Peptide Hormones, JA Parsons, Ed. 2-7.*
T Hanada and A Yoshimura. Regulation of cytokine signaling and inflamation. (2002) Cytokine and Growth Factor Reviews 13, 413-421.*
M.A. Adamus, et al. J. Cell. Biochem. (2001) 81, pp. 499-506.*
P. Rameshwar and P. Gascón. Blood. (1995) 86(2), pp. 482-490.*
P. Rameshwar, et al. Blood. (1993) 81(2), pp. 391-398.*
S.A. Bentley, et al. Bone Marrow Transplantation. (1997) 19, pp. 557-563.*
P. Rameshwar Clin. Immunol. Immunopath. (1997) 85(2), pp. 129-133.*

D.D. Joshi, et al. Blood (2001), 98(9), pp. 2697-2706.*
P. Rameshwar, et al. Blood. (2001) 97(10), pp. 3025-3031.*
Ahmad et al., "Dipeptidyl(amino)peptidase IV and Aminopeptidase M Metabolize Circulating Substance P *in Vivo*", J. Pharmacology and Experimental Therapeutics 1992 260(3):1257-1261.
Krause et al., "Structure, Functions, and Mechanisms of Substance P Receptor Action", J Invest Dermatol 1992 98:2S-7S.
Mentlein Rolf, "Dipeptidyl-peptidase IV (CD26) -role in the inactivation of regulatory peptides", Regulatory Peptides 1999 85:9-24.
Solan et al., "Soluble Recombinant Neutral Endopeptidase (CD10) as a Potential Antiinflammatory Agent", Inflammation 1998 22(1):107-121.
Stefano et al., "Inhibitory Effect of Morphine on Granulocyte Stimulation by Tumor Necrosis Factor and Substance P", Int. J. Immunopharmac. 1994 16(4):329-334.
van der Velden et al., "Cytokines and Glucocorticoids Modulate Human Bronchial Epithelial Cell Peptidases", Cytokine 1998 10(1):55-65.
van der Velden et al., "Peptidases:structure, function and modulation of peptide-mediated effects in the human lung", Clinical and Experimental Allergy 1999 29:445-456.
Vanhoof et al., "Proline motifs in peptides and their biological processing", FASEB J. 1995 9:736-744.
Rameshwar et al., "Hematopoietic Regulation Mediated by Interactions Among the Neurokinins and Cytokines", Leukemia and Lymphoma 1997 28:1-10.
Qian et al., "Effects of SP(1-4) on cobblestone-forming cells. Implications for endopeptidases as hematopoietic regulators", 10th International Congress of Immunology, Monduzzo Editore S.p.A.-Bologna Italy 575-5811.

* cited by examiner

*Primary Examiner*—Cecilia J. Tsang
*Assistant Examiner*—Andrew D. Kosar
(74) *Attorney, Agent, or Firm*—Licata & Tyrrell P.C.

(57) ABSTRACT

The present invention establishes the fact that the degradation of SP to SP(1-4) by endogenous NEP in BM stroma can be a mediator of hematopoietic stimulation by stem cell factor (SCF) and induce the production of TGF-β and TNF-α in BM stroma. The present invention establishes that compositions containing the SP(1-4) polypeptide, or NEP genetic elements, can be used to slow and or stop the rapid growth of stem and progenitor cells thus protecting them from the deleterious effects of cancer therapy. Hence, the polynucleotides and proteins of the present invention may be used to protect stem cells from the toxic effects of chemo- and radio-therapy, in those undergoing, or about to undergo such cancer related treatments. Also provided are compositions containing NEP antisense sequences and antibodies used for the increased proliferation and differentiation of stem and/or progenitor cells in those whom have already undergone chemo- and/or radio-therapy.

2 Claims, 10 Drawing Sheets

Clone 7:   1 catgacggtatcggtctcattacacccattgcacat 36
         AA:  1 HDGIGLITPIAH 12
NK-1 residues:       112 PIA 114

Clone 12:  1 gtcccaatttcgaaaacacccacagcagactcgcag 36
         AA:  1 VPISKTPTADSQ 12
NK-1 residues        392 SKTMT 396

Clone 19:  1 gtgacgacatctaagtagccgtatgtcctgagcccc 36
         AA:  1 VTTSK*PYVLSP 12
NK-1 residues:       271 PYI 273

Clone 23:  1 ctagatgttccgaatcaggcgacgctgattggagtt 36
         AA:  1 LDVPNQATLIGV 12
NK-1 residues:       22 PNQ 66

Clone 26:  1 cacccgtaagcataattgcgccttccctacgtagcg 36
         AA:  1 HP*A*1RLPYVA
NK-1 residues:       270 LPYI 273

Clone 28:  1 tacactcccgtcgcggcgtttccaacgcgttaagcc 36
         AA:  1 VTPVAAFPTR*A 12
NK-1residues:   110 FFPIAA 115

AA: amino acid

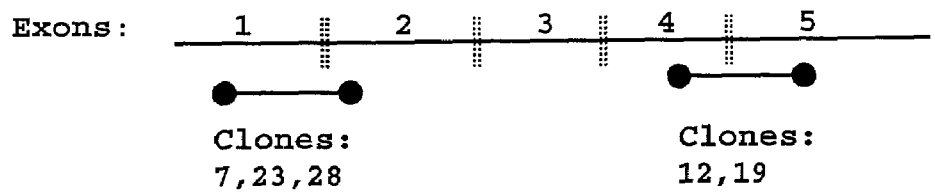

Exons:    1    2    3    4    5

Clones:            Clones:
7,23,28            12,19

Fig. 6

A.
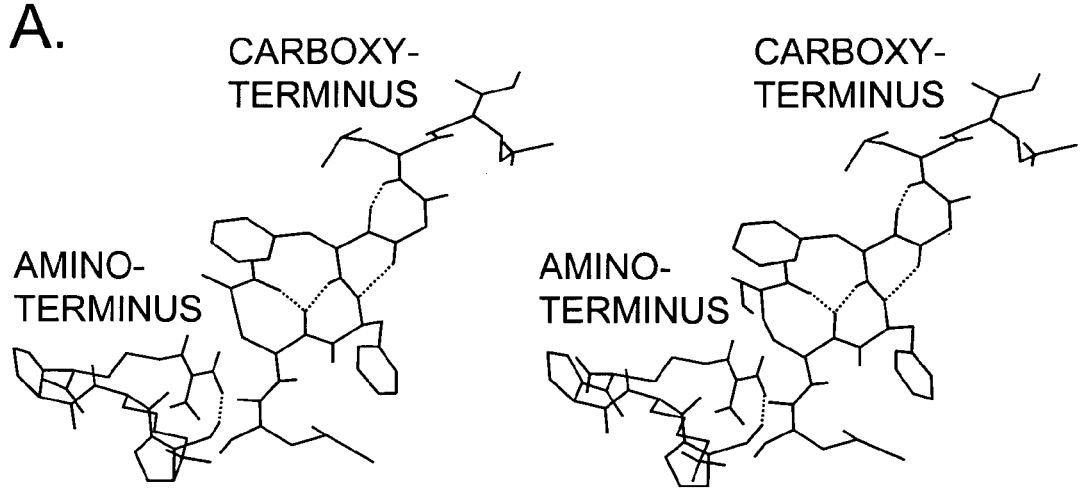
B.
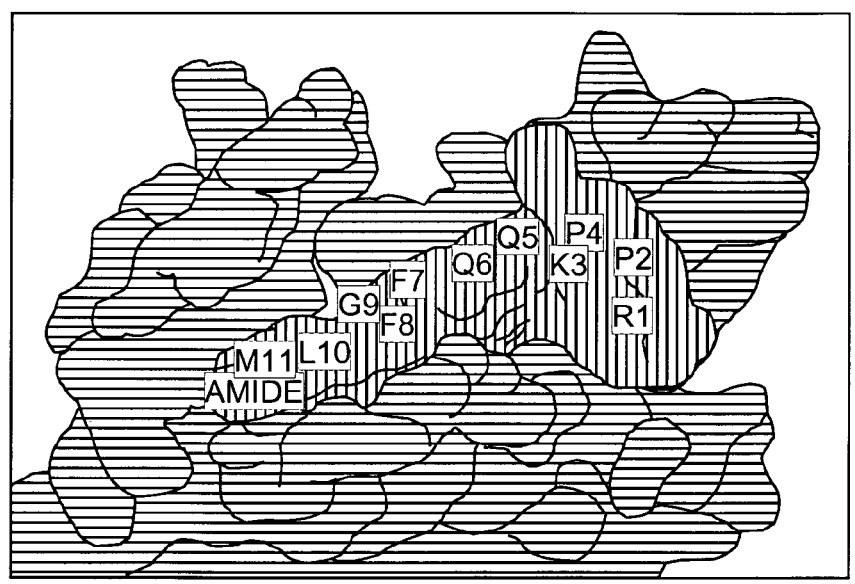
C.
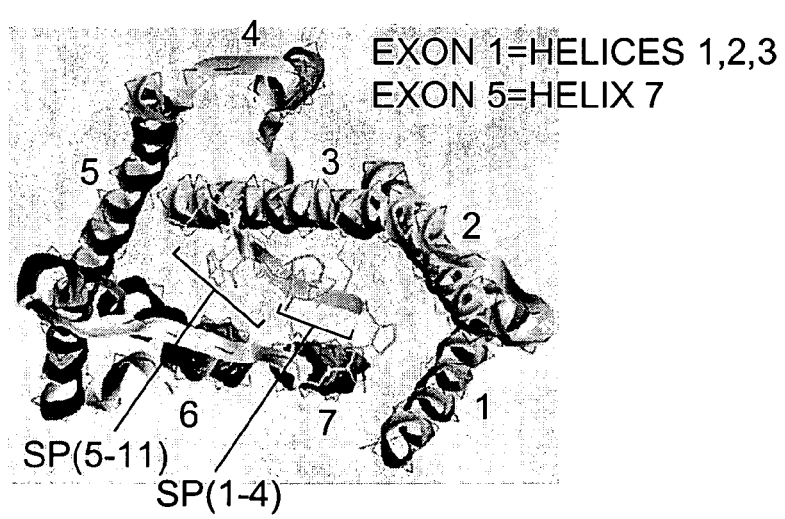
FIG. 8

AMINO TERMINAL SUBSTANCE P COMPOSITIONS AND METHODS FOR USING THE SAME

GOVERNMENT INTEREST

This invention was made with government support by the following Public Health Service grants: HL-54973 and HL-57675 from the National Institute of Health and CA89868 from the National Cancer Institute. The government may own certain rights in the present invention

FIELD OF THE INVENTION

The present invention relates to the field of molecular biology, immunology, and the regulation of stem cell proliferation and differentiation. In particular, this invention provides novel compositions and methods for protecting stem cells from chemo- and radio-therapeutic treatment. Specifically, this invention provides a novel composition of a Substance-P tetrapeptide, SP(1-4), which can be used to inhibit hemopoietic stem cell proliferation and differentiation into the various blood cells of the mature peripheral blood system and thereby act to protect stem cells from the toxic effects of chemo- and radio-therapy that targets rapidly dividing cells.

BACKGROUND OF THE INVENTION

Cells in the body are continually replaced. This can occur over a period of several hours up to many months. The presence of stem cells of various tissue types are present to grow and differentiate as a source of replacement cells for those cells that die. For example, the majority of blood cells are destined to die within a period of hours to weeks, depending on the specific blood cell type, and so must be continuously replaced. Bone Marrow (BM) is the major source of blood cells, including both white (lymphocytes, i.e., immune cells) and red blood cells (erythrocytes) in the adult.

Among the various cells that constitute the BM are primitive hematopoietic pluripotent stem cells, progenitor cells and stromal cells. Hemopoietic stem cells are a class of cells that have been defined functionally by the characteristics of extended self-renewal and the capacity to mature into one or more differentiated forms of blood cells, such as, lymphocytes, granulocytes, erythrocytes, megakaryocytes and stromal cells. Hence, an important property of stem cells is their ability to both proliferate, which ensures a continuous supply throughout the lifetime of an individual, and differentiate into the mature cells of the peripheral blood system.

Hematopoietic stem cells are present at about 0.01% of the bone marrow and serve as a source of replacement blood cells. When necessary, a pluripotent stem cell can begin to differentiate, and after successive divisions become committed, thus losing the capacity for self-renewal, to a particular line of development. A pluripotent hemopoietic stem cell, such as long term culture initiating cells (LTC-IC), can differentiate into either a lymphoid stem cell or a myeloid stem cell. The LTC-IC cells are one of the most primitive of cells and can potentially differentiate in any hematopoietic lineage.

Lymphoid stem cells can differentiate into a B-cell progenitor or a T-cell in the thymus. The B-cell progenitor formation is induced by Interleukin-7 (IL-7) or other differentiation factors, and is inhibited by TGF-β or Interleukin-4 (IL-4). The lymphoid stem cell can also differentiate into a T-cell progenitor cell that moves to the thymus wherein it differentiates into a pre-T-cell, followed by differentiation into a specific T-cell.

Myeloid stem cells may differentiate into a burst-forming unit-erythroid followed by a colony forming unit-erythroid or by further differentiation into a red blood cell induced by erythropoietin. Alternatively, a myeloid stem cell can differentiate into a colony forming unit-megakaryocyte followed by differentiation into a megakaryocyte that can then form platelets. Myeloid stem cells can also differentiate into a colony forming unit granulocyte macrophage (CFU-GM), which are the progenitors of monocytes and macrophages, colony forming unit eosinophil (CFU-E) or a colony forming unit basophil (CFU-B), which can then differentiate into eosinophils or basophils, respectively, under the control of GM-CSF/IL-3 or IL-3, respectively, and CFU-C cells. On the other hand, both TNF-α, TGF-β and TGF-β1 efficiently inhibit myeloid cell development (Zipori et al., 1986 and Broxmeyer et al., 1986) and TGF-β1 restricts lymphocyte proliferation (lee et al., 1986) and is a potent inhibitor of several proliferative activators for myelocytes and lymphoblasts including IL-3, G-CSF, GM-CSF (Masatsugu et al., 1987).

Virtually all of the circulating blood cells, including erythrocytes, leukocytes or lymphocytes, granulocytes and platelets originate from various progenitor cells that are themselves derived from precursor stem cells such as lymphoid and myeloid cells. Stem cells may also differentiate in to the supporting cells of the hemopoietic bone marrow matrix, such as stromal cells, that function in the formation and makeup of the hematopoietic microenvironment, which supports growth and differentiation of other hematopoietic stem cells into the various types of lymphoid and myeloid cells under the control of cytokines (described below).

Besides providing support these cells can also secrete multiple cytokines that have effects on the growth and/or differentiation of the lymphoid and myeloid progenitor cells. In addition, other cytokines (such as colony stimulating factors) can bind to stem cell growth supporting stromal cells and influence the types and concentrations of growth and/or differentiation factors secreted by the stromal cells.

Hematopoietic stem cell production, proliferation and differentiation occur in direct proximity to osteoblasts, a major component of the bone matrix, within the bone marrow cavity. The development of the bone marrow cavity is a coordinated process in which blood precursors migrate and colonize spaces carved out of embryonic bone and cartilage. Stromal cells like osteoblasts in the bone marrow, through adhesion events mediated by cell adhesion molecules (CAMs), such as integrins and selecting, provide the structural scaffolding for hematopoiesis, and also produce several of the soluble factors (cytokines) critical to the development of blood cells. Hence, the direct interaction of hematopoietic cells with osteoblasts stromal cells is important for maintaining hematopoiesis. Stromal cell-associated cytokines are expressed due to this interaction and stimulate blood cell proliferation and are involved in controlling the specific growth and differentiation of hematopoictic stem cells into the specific blood cell types.

The morphologically recognizable and functionally capable cells circulating in the blood include erythrocytes (red blood cells), leukocytes (white blood cells including both B and T cells), non B- and T-lymphocytes, phagocytes, neutrophilic, eosinophilic and basophilic granulocytes, and platelets. These mature cells are derived, on demand, from dividing progenitor cells, such as erythroblasts (for erythrocytes), lymphoid precursors, myeloblasts (for phagocytes including monocytes, macrophages and neutrophils), promyelocytes and myelocytes (for the various granulocytes) and megakaryocytes for the platelets. As stated above, these progenitor cells are themselves derived from lymphoid and myeloid precursor stem cells.

Many different proteins regulate cell viability, growth and differentiation of different hematopoietic cell lineages and play various roles in the molecular basis of abnormal cell development in blood-forming tissues. These regulators include cytokines such as colony stimulating factors and interleukins. Different cytokines can induce cell viability, multiplication and differentiation. Hematopoiesis is controlled by a network of interactions between these cytokines. This network includes positive regulators such as colony stimulating factors and interleukins and negative regulators such as transforming growth factor β (TGF-β) and tumor necrosis factors α and β (TNF). The functioning of this network requires an appropriate balance between these positive and negative regulators.

Hence, a complex network of cytokines as well as inter- and intra-cellular interactions regulate the proliferation and differentiation of a finite pool of hematopoietic stem cells. As described above, cytokines are protein growth factors that function as intercellular signals that regulate hematopoiesis, as well as local and/or systemic inflammatory responses, and include colony stimulating factors, interleukins and other growth factors having such activity.

Cytokines modulate target cells by interacting with cytokine receptors on the target cell. Principal cell sources of cytokines in vivo include T lymphocytes, B lymphocytes, macrophages, monocytes, platelets and stromal cells. While cytokine specific receptors are specific for a given cytokine, cytokine receptors are grouped into families based on shared features. The first group of cytokine receptors is the hemopoetin group which are present on cells including immune system cells that bind IL-2, IL-3, IL-4, IL-6 and IL-7. A second receptor family is the TNF receptor family which bind both TNF-α and TGF-β. A third family is the immunoglobulin (Ig) superfamily receptor family, which contain an Ig sequence-like motif and includes human IL-1 and IL-6 receptors.

Proliferation and differentiation of hematopoietic cells are regulated by hormone-like growth and differentiation factors designated as colony-stimulating factors (CSF) (Metcalf, D. Nature 339, 27–30 (1989)). CSF can be classified into several factors according to the stage of the hematopoietic cells to be stimulated and the surrounding conditions as follows: granulocyte colony-stimulation factor (G-CSF), granulocyte-macrophage colony-stimulation factor (GM-CSF), macrophage colony-stimulation factor (M-CSF), and interleukin 3 (IL-3).

Small amounts of certain hematopoietic growth factors account for the differentiation of stem cells into a variety of blood cell progenitors, for the tremendous proliferation of those cells, and for their differentiation into mature blood cells. For instance, G-CSF participates greatly in the differentiation and growth of neutrophilic granulocytes and plays an important role in the regulation of blood levels of neutrophils and the activation of mature neutrophils (Nagata, S., "Handbook of Experimental Pharmacology", volume "Peptide Growth Factors and Their Receptors", eds. Sporn, M. B. and Roberts, A. B., Spring-Verlag, Heidelberg, Vol.95/1, pp.699–722 (1990); Nicola, N. A. et al., Annu. Rev. Biochem. 58, pp.45–77 (1989)). It is also reported that G-CSF stimulates the growth of tumor cells such as myeloid leukemia cells. (Nicola and Metcalf, Proc. Natl. Acad. Sci. USA, 81, 3765–3769 (1984); Begley et al., Leukemia, 1, 1–8 (1987). Other growth factors include, erythropoietin (EPO), which is responsible for stimulating the differentiation of erythroblasts into erythrocytes and Macrophage-Colony Stimulating Factor (M-CSF) responsible for stimulating the differentiation of myeloblasts and myelocytes into monocytes.

Growth factors are part of the cytokine family of chemical messengers. As stated above, cytokines are among the factors that act upon the hematopoietic system to regulate blood cell proliferation and differentiation and they are also important mediators of the immune response being secreted by both B and T cells, as well as other various lymphocytes. Cytokines encourage cell growth, promote cell activation, direct cellular traffic, act as messengers between cells of the hematopoietic system, and destroy target cells (i.e., cancer cells). Among the various components involved in the modulation and regulation of the hematopoietic system that cytokines play a role in modulating are the tachykinins.

The tachykinins are immune and hematopoietic modulators that belong to a family of peptides encoded by the preprotachykinin-I (PPT-1) gene (Quinn, J. P., C. E. Fiskerstrand, L. Gerrard, A. MacKenzie, and C. M. Payne. 2000. Molecular models to analyze preprotachykinin-A expression and function. Neuropeptides 34:292–302). The tachykinins can be released in the BM and other lymphoid organs as neurotransmitters or from the resident BM immune cells (2–6). In the BM, PPT-I and other hematopoietic growth factors regulate expression of each other through autocrine and paracrine activities. It is believed that various cytokines induce the expression of the PPT-I gene in BM mesenchymal cells (Rameshwar, P. 1997. Substance P: A regulatory neuropeptide for hematopoiesis and immune functions. Clin. Immunol. Immunopath. 85:129–133.). The tachykinin family of peptides exerts pleiotropic functions such as neurotransmission and immune/hematopoietic modulation.

PPT-1 peptides exert both stimulatory and inhibitory hematopoietic effects by interacting with different affinities to the G-protein coupled receptors: NK-1, NK-2 and NK-3 (Krause, J. E., Y. Takeda, and A. D. Hershey. 1992. Structure, functions, and mechanisms of substance P receptor action. J. Invest. Dermatol. 98:2S-7S). NK-1 and NK-2 expression has been reported in BM cells (Rameshwar, P., A. Poddar, and P. Gascon. 1997. Hematopoietic regulation mediated by interactions among the neurokinins and cytokines. Leuk. Lymphoma 28:1–10). NK-1 is induced in BM cells by cytokines and other stimulatory hematopoietic regulators. NK-2 is constitutively expressed in BM cells that are unstimulated or stimulated with suppressive hematopoietic regulators. NK-1 and NK-2 are not co-expressed in BM cells because NK-1 induction by cytokines is correlated with the down regulation of NK-2. In BM cells, NK-1 expression requires cell stimulation whereas its expression in neural tissue is constitutive (Rameshwar, P. 1997. Substance P: A regulatory neuropeptide for hematopoiesis and immune functions. Clin. Immunol. Immunopath. 85:129–133, Yao, R., P. Rameshwar, R. J. Donnelly, and A. Siegel. 1999. Neurokinin-1 expression and colocalization with glutamate and GABA in the hypothalamus of the cat. Mol. Brain Res. 71:149–158, and Abrahams, L. G., M. A. Rerutter, K. E. McCarson, and V. S. Seybold. 1999. Cyclic AMP regulates the expression of neurokinin 1 receptors by neonatal rat spinal neurons. J. Neurochem. 73:50–58.). It is believed that a particular cytokine discriminates between the expression of NK-1 and NK-2, which directs the type of BM functions: stimulatory vs. inhibitory (Rameshwar, P., A. Poddar, and P.

Gascon. 1997. Hematopoietic regulation mediated by interactions among the neurokinins and cytokines. Leuk. Lymphoma 28:1–10).

Substance P (SP), the major tachykinin released in the BM, stimulates hematopoiesis through interactions with the neurokinin-1 (NK-1) receptor, which is resident on BM stroma, immune cells and other lymphoid organ cells. Hence, the expression of NK-1 determines the hematopoietic response of the tachykinins. NK-2 inhibits hematopoiesis by interacting with neurokinin-A, another tachykinin encoded for by the PPT-I gene. Recently, the present inventors have discovered that the stimulatory effects mediated by NK-1 can be changed to hematopoietic inhibition in the presence of the amino terminal of SP, a fragment found endogenously in the BM due to enzymatic digestion of SP by endogenous endopeptidases. Further, dysregulated expression of the PPT-1 gene has been associated with different pathologies such as cancer (Bost et al., 1992b; Henning et al., 1995; Ho et al., 1996; Michaels, 1998; Rameshwar et al., 1997a).

Under normal circumstances, the BM is able to respond quickly to an increased demand for a particular type of cell. The pluripotential stem cell is capable of creating and reconstituting all the cells that circulate in the blood, including both red and white blood cells and platelets. As stated, progenitor cells that derive from stem cells can replicate and differentiate rapidly. On average, 3–10 billion lymphocyte cells can be generated in an hour. The BM can increase this by 10 fold in response to need. However, in the throes of a diseased state, the BM may not produce enough stem cells, may produce too many stem cells or various ones produced may begin to proliferate uncontrollably.

Lymphoproliferative syndromes consist of several types of diseases known as leukemia and malignant lymphoma, which can further be classified as acute and chronic myeloid or lymphocytic leukemia, Hodgkin's lymphoma, and non-Hodgkin's lymphoma. These diseases are characterized by the uncontrollable multiplication or proliferation of leukocytes (primarily the B-cells), myelocytes and tissue of the lymphatic system, especially lymphocyte cells produced in the BM and lymph nodes.

Traditional methods of treating these leukemia related malignancies includes chemotherapy and radiotherapy. The theory behind chemo- and radio-therapies is that they take advantage of a cancerous cell's unnatural and vastly increased cell growth cycle. Once adulthood is reached, the majority of cells within the body grow and proliferate for the purposes of replacing old and dying cells. As a consequence of this, the majority of the body's terminally differentiated cells are either not in a growth phase in their cell cycle or if they are it is at a slow rate. Hence, for example, cells of the skin and liver have a very slow growth rate, while cells of the kidneys grow so slow in the adult as to be non-existant. Cancerous cells, on the other hand, have a very rapid growth rate in which large amounts of DNA is synthesized and the cell's membrane becomes more permeable to extracellular elements. Due to this rapid growth and increased cell-surface permeability, cancerous cells are more susceptible to the effects of DNA degrading chemo- and radio-therapeutic agents that disrupt DNA synthesis and cause cell death. Because most cells of the body grow, if at all, at a slower rate they are not as susceptible to the toxic effects of chemo- and radio-therapy.

Problems arise however with regard to those cells of the body that naturally have increased rates of proliferation such as stem cells, progenitor cells and the many different hemopoietic cells of the immune system. Chemo- and radio-therapeutic agents do not distinguish between the aberrant cancerous cells and the rapid growing, but normal stem and immune cells. Hence, both tumor and healthy stem and immune cells are killed off by the administration of chemo- and radio-therapeutic toxic agents. This leads to a drop in blood count, suppression of the immune response, and to an increased risk of bacterial and/or fungal infection, which can lead to death.

Because stem and progenitor cells, like cancer cells, have an increased sensitivity to the toxic effects of chemo- and radio-therapy, and because chemo- and radio-therapeutic agents are indiscriminate when they assault cells of the body, leading to a compromised immune system, there has been, and continues to be, a long felt need for a way to protect the healthy stem and progenitor cells of the body from the toxic effects of chemo- and radio-therapy.

The present invention includes novel compositions and methods for slowing, and or turning off, stem and progenitor cell growth in a subject, specifically, in a subject about to undergo toxic cancer treatment, thus protecting these cells from the highly toxic effects associated with chemo- and radio-therapy. The Applicants have discovered that neutral endopeptidase (NEP) utilizes Substance P (SP) to produce a tetrapeptide, SP(1-4), that inhibits proliferation of lymphoid-myeloid stem and progenitor cells. It has been determined, through its interactions with TGF-$\beta$ and TNF-$\alpha$, that SP(1-4) can be used as an effective treatment to shield both stem and progenitor cells from the toxic effects of chemo- and radio-therapy thereby protecting a subject's immune system from being compromised and reducing the risk of bacterial or fungal infection, allowing for a greater dosage of chemo- and/or radio-therapy to be administered and/or over a longer administration period, as well as shortening the recovery period required for new stem cell growth and terminal blood cell replenishment.

SUMMARY OF THE INVENTION

The bone marrow (BM) is the major organ where stem cells grow, develop and differentiate into the mature cells of the peripheral blood system. Homeostasis in the BM is maintained by inter- and intra-cellular interactions by the various subsets of BM cells. An understanding of normal BM functions has been extended to unravel a novel mechanism for BM-derived hemopoietic stem cell proliferation, differentiation and/or its inhibition. The present invention discloses the isolation and purification of a novel peptide SP(1-4), from stimulated BM stromal cells, that inhibits the proliferation of both lymphoid and myeloid stem and progenitor cells. Applicants discovered that endogenous neutral endopeptidase (NEP) utilizes SP as substrate to produce a novel peptide SP(1-4), which can be used in accordance with the compositions and methods of the present invention to protect stem cells from the evasive effects of chemo- and radio-therapy undergone by those suffering from hyperproliferative blood diseases such as leukemia, lymphoma, and other blood related cancers.

Based on the methods of the present invention it has been determined, given that SP and SP(1-4) interact with the same receptor to mediate opposing hematopoietic effects, that SP(1-4) may be administered to competitively inhibit the effects of SP on both stem and progenitor cell proliferation and differentiation. Furthermore, based on the experimental procedures herein detailed, it has been determined that SP(1-4) may be administered to induce production of TGF-$\beta$ and TNF-$\alpha$ thereby potentiating the effects of these two cytokines in BM stroma; namely, to increase their antiinflammatory effect. Further still, based on the interaction of NEP on SP, it has been hypothesized that the cellular delivery of NEP related genes and/or proteins may be used to either increase and/or decrease NEP expression, thereby either decreasing stem cell differentiation, by degrading SP to SP(1-4) and thereby protecting stem cells, or increasing cell differentiation, by inhibiting endogenous NEP from degrading SP, and thereby promoting cell differentiation for increased production of the mature cells of the peripheral blood system, which would be useful in the treatment of myelopriliferative disorders such as leukemia and lymphoma.

These discoveries led to the compositions and methods of the present invention. Hence, the present invention provides novel compositions that include the SP(1-4) peptide and/or NEP genetic sequences, for the regulation and protection of hemtaopoietic stem and progenitor cell proliferation, as well as for the induction of the various effects of TGF-β and TNF-α, specifically those effects related to anti-inflammation.

According to one aspect of this invention, a pharmaceutically acceptable composition containing an SP(1-4) therapeutic is provided. Such a therapeutic may include an isolated and purified polynucleotide that has at least 70% identity to SEQ ID NO:1 and preferably includes a nucleotide sequence that is identical to that of SEQ ID NO:1. Further, such a therapeutic may also include an isolated and purified SP(1-4) polypeptide that is substantially similar to that of SEQ ID NO:2 and preferably is identical to that of SEQ ID NO:2. Additionally, such a therapeutic composition will include a pharmaceutically acceptable carrier, which are well known in the art and described below.

Another aspect of this invention features pharmaceutically acceptable compositions containing a NEP therapeutic. Such a therapeutic may include an isolated NEP polynucleotide, antisense sequence, protein, protein fragments and/or antibodies immunospecific to the protein, or one or more epitopes thereof. Specifically, such a composition may include a biologically effective amount of a NEP polynucleotide substantially similar to that of SEQ ID NO:3, and preferably is identical to SEQ ID NO:3, along with an acceptable carrier. However, dependent upon the results desired, such a composition may include a biologically effective amount of a NEP polynucleotide sequence that is the antisense sequence to SEQ ID NO:3, along with an acceptable carrier. Further, such a composition may include a biologically effective amount of an antibody immunospecific for the NEP protein comprising the amino acid sequence of SEQ ID NO:4, and an acceptable carrier.

A further embodiment of the present invention provides methods for protecting stem cells of those either undergoing or about to undergo cancer therapy. These methods include the administration of the pharmaceutical compositions described above. Specifically, a method of protecting stem cells is provided that includes the administration of a biologically effective amount of a SP(1-4) polypeptide or NEP polynucleotide and an acceptable carrier. These methods are effective for the protection of such stem cells as lymphoid, myeloid, LTC-IC, CFU-GM, CFU-E, CFU-B, CFU-C, burst-forming unit-erythroid cell, colony forming unit-erythroid and colony forming unit-megakaryocyte cells.

A further aspect of the present invention provides methods for increasing stem cell growth. These methods include the administration of a pharmaceutical composition either containing a biologically effective amount of a polynucleotide coding for the antisense sequence to SEQ ID NO:3, and an acceptable carrier, or containing a biologically effective amount of an antibody immunospecific for the NEP polypeptide, comprising the amino acid sequence of SEQ ID NO:4 and an acceptable carrier. These methods will be useful for down regulating the activity of endogenous NEP and will thereby increase the activity of SP in promoting stem cell growth and differentiation.

Also provided is a vector for the delivery of a NEP therapeutic to a stem cell for the protection or rapid growth of stem cells, wherein the vector contains an expression cassette encoding the NEP therapeutic which may be a NEP polynucleotide, a NEP polynucleotide antisense sequence, a NEP protein, or an antibody immunospecific to the NEP protein.

As an additional aspect of the present invention a method is provided for increasing the intracellular production of TGF-β and TNF-α by the administration of a SP(1-4) composition. Such a composition may be useful for potentiating and enhancing the effects commonly associated with TGF-β and TNF-α. For instance, an SP(1-4) composition may be administered in situations where the enhanced effects of either TGF-β or TNF-α are desired, specifically for the purposes of reducing inflammation.

BRIEF DESCRIPTION OF THE DRAWINGS

The invention is best understood from the following detailed description when read in connection with the accompanying drawings, in which:

FIG. 6. Selected clones from a random dodecapeptide library, screened with SP(1-4): Shown are the amino acid residues of the DNA sequence for each clone. Bold and underlined residues indicate regions that align with NK-1 (top). Alignment of the combined amino acid sequences from the peptide library with NK-1, Accession #: m76675 (bottom).

FIG. 8. A. Steric view of SP. Yellow dashed lines represent hydrogen bonds. B. Overhead view of SP binding to NK-1 represented as solvent accessible surfaces. Colors represent electrostatic potential, with red as positive and blue, negative. C. Overhead view of SP binding to NK-1 with the binding domains shown for SP(1-4).

DETAILED DESCRIPTION OF THE INVENTION

Introduction

Figure 1:
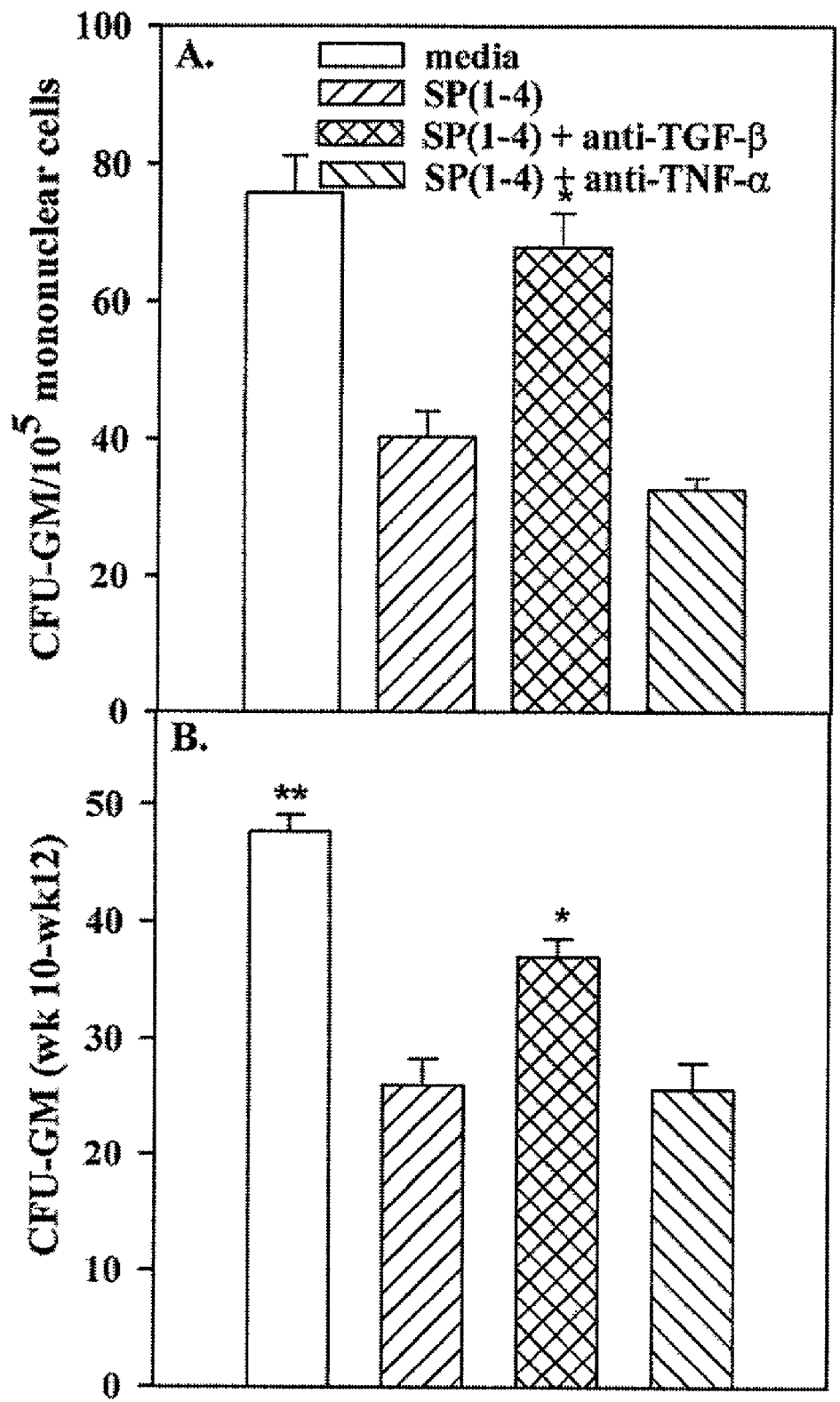
FIG. 1. Role of TGF-β and TNF-α in the suppression of CFU-GM and LTC-IC proliferation by SP(1-4). Clonogenic (A) and LTC-IC (B) assays were performed in the presence of 10 nM SP(1-4). Parallel cultures contained anti-TGF-β or anti-TNF-α. The results are expressed as the mean±SD of six experiments, each performed with a different healthy BM donor. *p<0.05 vs. SP(1-4) alone; **p<0.05 vs. SP(1-4)+ anti-TGF-β.

In the adult, the bone marrow (BM) is the major site of hematopoiesis. Biological activities in the BM are complex albeit controlled through cell-cell interactions among the hematopoietic stem cell, progenitors, mesenchymal cells and accessory cells[1]. Cellular interactions in the BM can lead to the induction of soluble, hematopoietic regulators such as cytokines, neuropeptides and neurotrophic factors[2]. Other hematopoietic regulators can be derived as neurotransmitters from the innervated nerve fibers in the BM, and as hormones from the peripheral circulation[2]. Despite the distant source of hormones, they modulate biological responses in the BM through specific receptors on resident BM cells[3].

The general consensus is that a finite pool of hematopoietic stem cells produces mature immune and blood cells through a complex, but controlled network that includes cells and soluble factors. Regardless of the pathways that lead to hematopoietic stimulation, the process of feedback is important in maintaining homeostasis and protecting the pool of hematopoietic stem cell. Understanding this dynamic process in the BM could have an impact on several clinical areas such as gene therapy, chemotherapy and BM transplant[4]. Herein below is described a model explaining the mechanism for negative feedback by the amino terminal of substance P, SP(1-4) on the effects of two hematopoietic stimulators: stem cell factor (SCF) and SP. These two stimulators regulate the induction of each other in BM cells[2,5]. SP(1-4) is derived from degradation of SP by endogenous endopeptidases in the BM[6,7].

SP, an undecapeptide is evolutionary conserved and is the major peptide derived from the preprotachykinin-I (PPT-I) gene[9,10]. PPT-I peptides exert both stimulatory and inhibitory hematopoietic effects[5], which are mediated through G-protein coupled receptors: NK-1, NK-2 and NK-3[5,11,12]. NK-1 is induced in BM cells by cytokines and other stimulatory hematopoietic regulators[2]. NK-2 is constitutively expressed in BM cells that are unstimulated or stimulated with suppressive hematopoietic regulators[5]. NK-1 and NK-2 are not co-expressed in BM cell since NK-1 induction by cytokines is correlated with the down regulation of NK-2[3,5].

Endopeptidases are ubiquitously expressed in hematopoietic cells[7]. Dipeptidyl-peptidase IV (CD26/DPP IV) aminopeptidase P/APP, angiotensin converting enzyme/ACE and neutral endopeptidase (NEP)/CD10 utilize SP as their substrates[6,7,13,14]. The carboxyl portion of the truncated peptide can be further digested by aminopeptidases N/CD13[15,16] resulting in Arg-Pro and Arg-Pro-Lys-Pro: SP(1-4) (SEQ ID NO:2) Hence, cytokines, SP and endopeptidases regulate the expression of each other in BM cells[13,14,17]. The proinflammatory properties of SP and cytokines have been linked to the activities of various endopeptidases[14,17].

Based on the methods of the present invention it has been determined that NEP uses SP as a substrate, degrading the mature form of the protein to SP(1-4). Further, it has been determined that SP and SP(1-4) interact with the same receptor, NK-1. However, because SP(1-4) is only a truncated form of the mature protein, it is unable to elicit the same morphological response from binding to the receptor and therefore acts as a competitive inhibitor of the effects of SP on both stem and progenitor cell proliferation and differentiation.

Hence, the present invention discloses the isolation and purification of a novel peptide SP(1-4), that inhibits the proliferation of both lymphoid and myeloid stem and progenitor cells. The present inventors have discovered that SP(1-4) can be used in accordance with the compositions and methods of the present invention, as described below, to protect stem cells from the evasive effects of chemo- and radio-therapy undergone by those suffering from hyperproliferative blood diseases such as leukemia, lymphoma, and other blood related cancers for which chemo- and/or radio-therapy may be sought.

Definitions

Various terms relating to the biological molecules of the present invention are used throughout the specification and claims.

The term "stem cell" in the context of the present invention, refers to any cell capable of further differentiation or development, from which further differentiation or development results in increased specialization or modification of the phenotype of the stem cell or tissue, or progeny thereof. Such stem cells are derived from cells of mesodermal, endodermal or ectodermal origin and may include such cells as: LTC-IC, CFU-GM, CFU-E, CFU-B, burst-forming unit-erythroid cell, colony forming unit-erythroid and colony forming unit-megakaryocyte cells.

By the term "hemopoiesis" or "hematopoiesis" is intended the production of cellular elements of the blood from hemopoietic progenitor and stem cells, initially as myeloid and lymphoid cells and their progeny, and further includes, but is not limited to, megakaryocytopoiesis, myelopoiesis, lymphopoiesis, eosinophilpoiesis, neutrophilpoiesis, T-cell production, B-cell production, platelet production, basophil production and erythropoiesis and monocyte production.

The terms "hemopoietic stem cell", "hematopoietic progenitor cell" or "hemopoietic bone marrow cell" refers to a cell in any of the blood cell lineages (e.g., myeloid, monocytoid, basophil, neutrophil, erythroid, lymphoid, megakaryocytoid) that is a precursor of the mature blood or lymph cell or stromal cell. The term as used herein is intended to also include very early precursors such as pluripotent stem cells that are both self-renewing and give rise to all lineages and stromal cells as well as committed stem cells, which may have more limited self-renewal capacity than pluripotent stem cells and are committed to a particular cell lineage.

Also, pluripotent stem cells are targets of the methods of the present invention. For example, myeloid stem cells which are thought to be derived from the committed stem cells of the myeloid lineage, are considered to be targets of the methods of the present invention, which may also include, but is not limited to precursor cells of red blood cells (RBCs), platelets, monocytes, neutrophils, basophilsand eosinophils. For a brief description of hematopoietic cell development/differentiation, see, e.g., Metcalf et al., J. Cell. Physiol. 116:198 (1983).

The term "stromal cell" refers to a heterogeneous population of cells naturally present in the bone marrow. Stromal cells may include, as non-limiting examples, cells derived from the bone marrow which are referred to as at least one of adipocytes, preadipocytes, fibroblasts, fibroblast colony forming units (CFU-F), osteoblasts, reticular cells and macrophages. Cloned stromal cell lines derived from such cells are also contemplated to be within the scope of the present invention (see, e.g., Dorshkind (Ann. Rev. Immunol. 8:111–137 (1990)), which is entirely incorporated herein by reference.

"SP(1-4)" refers generally to a tetrapeptide, Arg-Pro-Lys-Pro (SEQ ID NO:2) that is the result of degradation of SP to SP(1-4) by endopeptidases such as, for example, endogenous neutral endopeptidase (NEP). SP(1-4) has an expression that coincides with the competitive inhibition of SP, the upregulation of NEP and the induction of TGF-β and TNF-α, in accordance with the present invention, which is described in detail herein and throughout the specification.

"NEP" refers generally to a neutral endopeptidase protein that is responsible for converting active SP to an inactive form comprising SP(1-4).

"NEP activity or NEP polypeptide activity" or "biological activity of the NEP or NEP polypeptide" refers to the metabolic or physiologic function of said NEP to convert SP into SP (1-4) including similar activities or improved activities or these activities with decreased undesirable side effects.

"NEP gene" refers to a polynucleotide as defined below in accordance with the present invention, which encodes an NEP polypeptide.

A "SP(1-4) therapeutic" refers to a therapeutically effective amount of an SP(1-4) polypeptide suitable for inhibiting the effects of SP and/or potentiating the effects of TGF-β or TNF-α.

A "NEP therapeutic" refers to a therapeutically effective amount of a NEP related genetic sequence such as, but not limited to polynucleotide, polynucleotide antisense sequence, and NEP peptide, protein or protein fragment.

"Isolated" means altered "by the hand of man" from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide separated from the coexisting materials of its natural state is "isolated", as the term is employed herein.

"Polynucleotide" generally refers to any polyribonucleotide or polydeoxyribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA.

The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications have been made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the gene-encoded amino acids. "Polypeptides" include amino acid sequences modified either by natural processes, such as posttranslational processing, or by chemical modification techniques that are well known in the art. Such modifications are well described in basic texts and in more detailed monographs; as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from posttranslation natural processes or may be made by synthetic methods.

Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, Proteins—Structure And Molecular Properties, 2nd Ed., T. E. Creighton, W. H. Freeman and Company, New York, 1993 and Wold, F., "Posttranslational Protein Modifications: Perspectives and Prospects, pgs. 1–12 in "Posttranslational Covalent Modification Of Proteins", B, C. Johnson, Ed., Academic Press, New York, 1983; Seifter et al., "Analysis for protein modifications and nonprotein cofactors", Meth Enzymol (1990) 182:626–646 and Rattan et al., "Protein Synthesis: Posttranslational Modifications and Aging", Ann AIY Acad Sci (1992) 663:48–62.

"Variant" as used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical.

A variant and reference polypeptide may differ in amino acid sequence by one or more substitutions, additions, and deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis. For instance, a conservative amino acid substitution may be made with respect to the amino acid sequence encoding the polypeptide.

A "conservative amino acid substitution", as used herein, is one in which one amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

The term "substantially the same" refers to nucleic acid or amino acid sequences having sequence variation that do not materially affect the nature of the protein (i.e. the structure, stability characteristics, substrate specificity and/or biological activity of the protein). With particular reference to nucleic acid sequences, the term "substantially the same" is intended to refer to the coding region and to conserved sequences governing expression, and refers primarily to degenerate codons encoding the same amino acid, or alternate codons encoding conservative substitute amino acids in the encoded polypeptide. With reference to amino acid sequences, the term "substantially the same" refers generally to conservative substitutions and/or variations in regions of the polypeptide not involved in determination of structure or function.

The term "substantially pure" refers to a "preparation comprising at least 50–60% by weight the compound of interest (e.g., nucleic acid, oligonucleotide, protein, etc.). More preferably, the preparation comprises at least 75% by weight, and most preferably 90–99% by weight, the compound of interest. Purity is measured by methods appropriate to the compound of interest (e.g. chromatographic methods, agarose or polyacrylamide gel electrophoresis, HPLC analysis, and the like).

The term "expression cassette" refers to a nucleotide sequence that contains at least one coding sequence along with sequence elements that direct the initiation and termination of transcription. An expression cassette may include additional sequences, including, but not limited to promoters, enhancers, and sequences involved in post-transcriptional or post-translational processes.

The term "operably linked" or "operably inserted" means that the regulatory sequences necessary for expression of the coding sequence are placed in a nucleic acid molecule in the appropriate positions relative to the coding sequence so as to enable expression of the coding sequence. This same definition is sometimes applied to the arrangement other transcription control elements (e.g. enhancers) in an expression vector.

Transcriptional and translational control sequences are DNA regulatory sequences, such as promoters, enhancers, polyadenylation signals, terminators, and the like, that provide for the expression of a coding sequence in a host cell.

The terms "promoter", "promoter region" or "promoter sequence" refer generally to transcriptional regulatory regions of a gene, which may be found at the 5' or 3' side of the coding region, or within the coding region, or within introns. Typically, a promoter is a DNA regulatory region capable of binding RNA polymerase in a cell and initiating transcription of a downstream (3' direction) coding sequence. The typical 5' promoter sequence is bounded at its 3' terminus by the transcription initiation site and extends upstream (5' direction) to include the minimum number of bases or elements necessary to initiate transcription at levels detectable above background. Within the promoter sequence is a transcription initiation site (conveniently defined by mapping with nuclease S1), as well as protein binding domains (consensus sequences) responsible for the binding of RNA polymerase.

A "vector" is a replicon, such as plasmid, phage, cosmid, or virus to which another nucleic acid segment may be operably inserted so as to bring about the replication or expression of the segment.

The term "nucleic acid construct" or "DNA construct" is sometimes used to refer to a coding sequence or sequences operably linked to appropriate regulatory sequences and inserted into a vector for transforming a cell. This term may be used interchangeably with the term "transforming DNA". Such a nucleic acid construct may contain a coding sequence for a gene product of interest, along with a selectable marker gene and/or a reporter gene.

A "heterologous" region of a nucleic acid construct is an identifiable segment (or segments) of the nucleic acid molecule within a larger molecule that is not found in association with the larger molecule in nature. Thus, when the heterologous region encodes a mammalian gene, the gene will usually be flanked by DNA that does not flank the mammalian genomic DNA in the genome of the source organism. In another example, a heterologous region is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

The term "DNA construct", as defined above, is also used to refer to a heterologous region, particularly one constructed for use in transformation of a cell. A cell has been "transformed" or "transfected" or "transduced" by exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA.

The term "in vivo delivery" involves the use of any gene delivery system, such as viral- and liposome-mediated transformation for the delivery and introduction of a therapeutic agent to the cells of a subject while they remain in the subject. Such therapeutic agents may include, for example, NEP DNA, cDNA, RNA, and antisense polynucleotide sequences.

As used herein, the term "transduction," is used to describe the delivery of DNA to eukaryotic cells using viral mediated delivery systems, such as, adenoviral, AAV, retroviral, or plasmid delivery gene transfer methods. Preferably the viral mediated delivery system is targeted specifically to the cell, wherein delivery is sought. The production of targeted delivery systems is well known and practiced in the recombinant arts. A number of methods for delivering therapeutic formulations, including DNA expression constructs (as described further below), into eukaryotic cells are known to those skilled in the art. In light of the present disclosure, the skilled artisan will be able to deliver the therapeutic agents of the present invention to cells in many different but effective ways. For instance, the specificity of viral gene delivery may be selected to preferentially direct the NEP gene to a particular target cell, such as by using viruses that are able to infect particular cell types (i.e., leukemia cells). Naturally, different viral host ranges will dictate the virus chosen for gene transfer.

"In vitro gene delivery" refers to a variety of methods for introducing exogenous DNA into a cell that has been removed form its host environment.

As used herein the term, "transfection" is used to describe the delivery and introduction of a therapeutic agent to a cell using non-viral mediated means, these methods include, e.g., calcium phosphate- or dextran sulfate-mediated transfection; electroporation; glass projectile targeting; and the like. These methods are known to those of skill in the art, with the exact compositions and execution being apparent in light of the present disclosure.

"Ex vivo gene delivery" refers to the procedure wherein appropriate cells are removed form the host organism, transformed, transduced or transfected in accordance with the teachings of the present invention, and replaced back into the host organism, for the purpose of therapeutic restoration and/or prevention.

"Delivery of a therapeutic agent" may be carried out through a variety of means, such as by using parenteral delivery methods such as intravenous and subcutaneous injection, and the like. Such methods are known to those of skill in the art of drug delivery, and are further described herein in the sections regarding pharmaceutical preparations and treatment. Compositions, include pharmaceutical formulations, comprising a NEP gene, protein, antisense polynucleotide sequence or antibody immunospecific with NEP, SP(1-4) polypeptides that may be delivered by means well known in the art and described below. In such compositions, the NEP may be in the form a DNA segment, recombinant vector or recombinant virus that is capable of expressing a NEP protein in a cell; specifically, a BM cell. These compositions, including those comprising a recombinant viral gene delivery system, such as an adenovirus particle, may be formulated for in vivo administration by dispersion in a pharmacologically acceptable solution or buffer. Preferred pharmacologically acceptable solutions include neutral saline solutions buffered with phosphate, lactate, Tris, and the like.

The term "contacted" when applied to a cell is used herein to describe the process by which an NEP gene, protein, antisense sequence antibody immunospecific for NEP, and/or an SP(1-4) polypeptide, is delivered to a target cell or is placed in direct proximity with the target cell. This delivery may be in vitro or in vivo and may involve the use of a recombinant vector system. Any method may be used to contact a cell with the NEP associated protein or nucleotide sequence or SP(1-4) polypeptide, so long as the method results in either increased or decreased levels of functional NEP protein within the cell and/or the decreased functionality of endogenous SP.

With reference to NEP the term "contacted" includes both the direct delivery of a NEP protein to the cell and the delivery of a gene or DNA segment that encodes NEP, or its antisense polynucleotide sequence, which gene or antisense sequence will direct or inhibit, respectfully, the expression and production of NEP within the cell.

Since protein delivery is subject to drawbacks, such as degradation and low cellular uptake, it is contemplated that the use of a recombinant vector that expresses a NEP protein, or encodes for an NEP polynucleotide antisense sequence, will be of particular advantage for delivery.

"Antibodies" as used herein includes polyclonal and monoclonal antibodies, chimeric, single chain, and humanized antibodies, as well as Fab fragments, including the products of a Fab or other immunoglobulin expression library. With respect to antibodies, the term, "immunologically specific" refers to antibodies that bind to one or more epitopes of a NEP protein, but which do not substantially recognize and bind other molecules in a sample containing a mixed population of antigenic biological molecules.

The term "specific binding affinity" is meant that the antibody or antibody fragment binds to target compounds (i.e., NEP) with greater affinity than it binds to other compounds under specified conditions. Antibodies or antibody fragments having specific binding affinity to a compound may be used to inhibit the function of that compound by contacting it with the antibody or antibody fragment under conditions such that an immunocomplex forms inihibiting the function of the compound conjugated to the antibody or antibody fragment.

The term "polyclonal" refers to antibodies that are heterogeneous populations of antibody molecules derived from the sera of animals immunized with an antigen or an antigenic functional derivative thereof. For the production of polyclonal antibodies, various host animals may be immunized by injection with the antigen. Various adjuvants may be used to increase the immunological response, depending on the host species.

"Monoclonal antibodies" are substantially homogenous populations of antibodies to a particular antigen. They may be obtained by any technique that provides for the production of antibody molecules by continuous cell lines in culture. Monoclonal antibodies may be obtained by methods known to those skilled in the art. See, for example, Kohler, et al., Nature 256:495–497, 1975, and U.S. Pat. No. 4,376, 110.

The term "antibody fragment" refers to a portion of an antibody, often the hypervariable region and portions of the surrounding heavy and light chains, that displays specific binding affinity for a particular molecule. A hypervariable region is a portion of an antibody that physically binds to the target compound. The term "antibody fragment" also includes single charge antibodies.

With respect to "therapeutically effective amount" is an amount of the NEP polynucleotide, NEP antisense polynucleotide or NEP polypeptide or protein, antibody immunospecific for NEP, or SP(1-4) polypeptide, that when administered to a subject is effective to bring about a desired effect (e.g., an increase or decrease in progenitor cell maturation, differentiation and/or proliferation) within the subject.

Polypeptides

As described herein, above and below, SP fragments exert immune and hematopoietic regulation[18,19]. The herein described methods show that SP(1-4) inhibits the proliferation of late and early hematopoietic progenitors. The 'parent' peptide, SP and cytokines associated with hematopoietic stimulation regulate the expression of each other leading to positive hematopoiesis[2]. The present invention involves the digestion of SP to SP(1-4) as a mechanism of hematopoietic feedback on the effects of SCF. This particular cytokine represents a model hematopoietic stimulator, which interacts with SP to regulate the expression of each other[20,21]. Induction of negative hematopoietic regulators, TGF-β and TNF-α, the receptors for SP and its fragments (NK-1 and NK-2) and induction of NEP mRNA by SP/SP(1-4)-NK-1/NEP interactions were examined in timeline proteomic studies.

A novel mechanism in which the PPT-I gene could be involved in modulating hematopoiesis, and indirectly inhibiting stem cell growth was discovered. In the BM, SP(1-4) could be derived through enzymatic digestion by endogenous endopeptidases[6,7], such as NEP. Through the present studies it was determined that SP(5-11) exerts stimulatory effects similar to the parent peptide[8], however, the effects of the amino terminal fragment raised the question of SP(1-4) being effective as a hematopoietic feedback inhibitor. The experimental evidence suggested that SP(5-11) might be quickly degraded to a non-functional form by other endopeptidases that can use the longer carboxyl fragment as a substrate[15,16].

Figure 2:
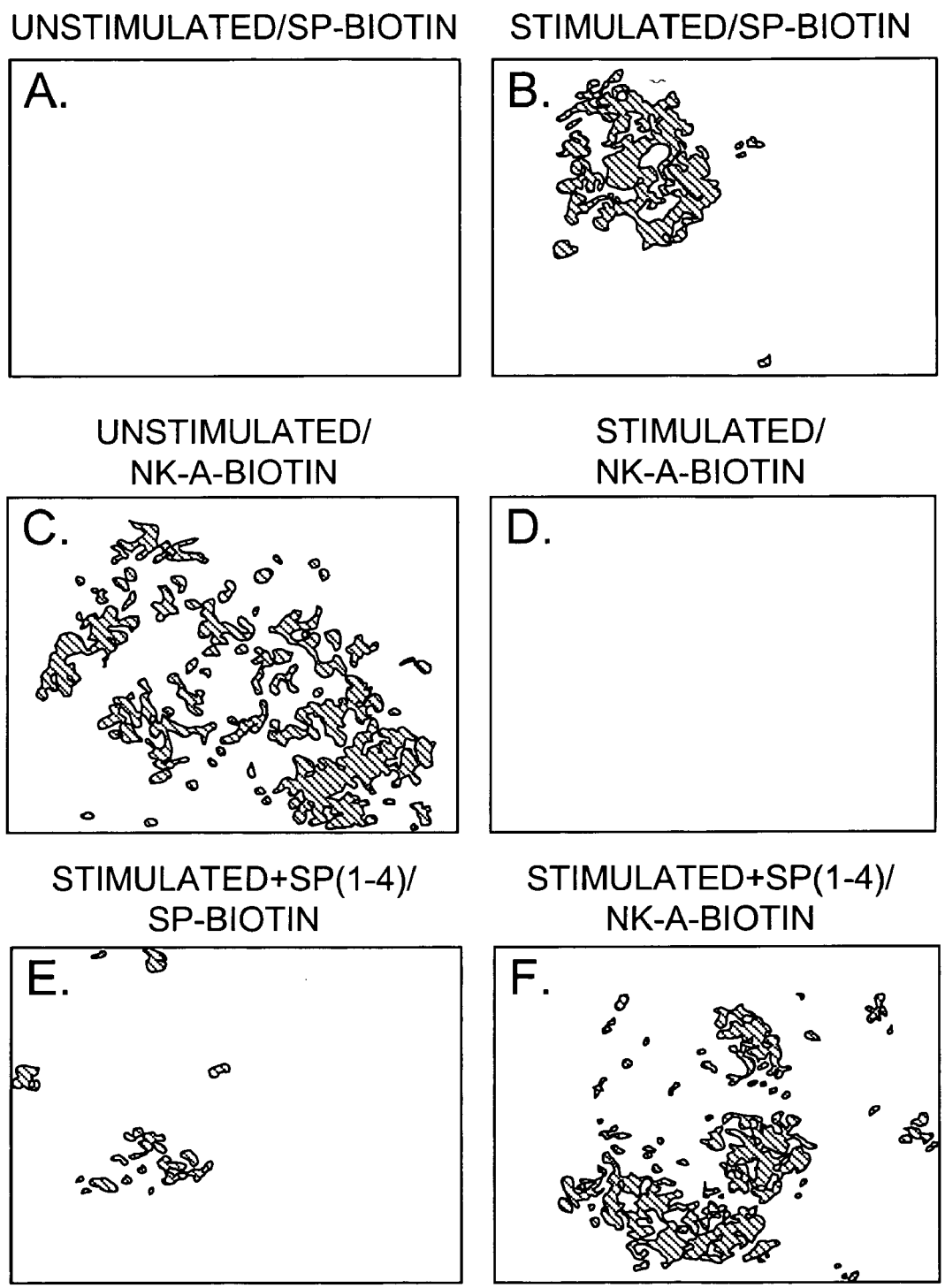
FIG. 2. Immunofluorescence for SP- and NK-A-binding sites in BM stroma. Cells were stimulated with 10 ng/ml SCF and/or 10 nM SP(1-4) for 24 h. After this, cells were labeled with biotin-SP or biotin-NK-A and then developed with FITC-Avidin. Unstimulated (A and C); SCF-stimulated (B and D); Consecutive stimulation with SCF and SP(1-4) (E and F).
Figure 5:
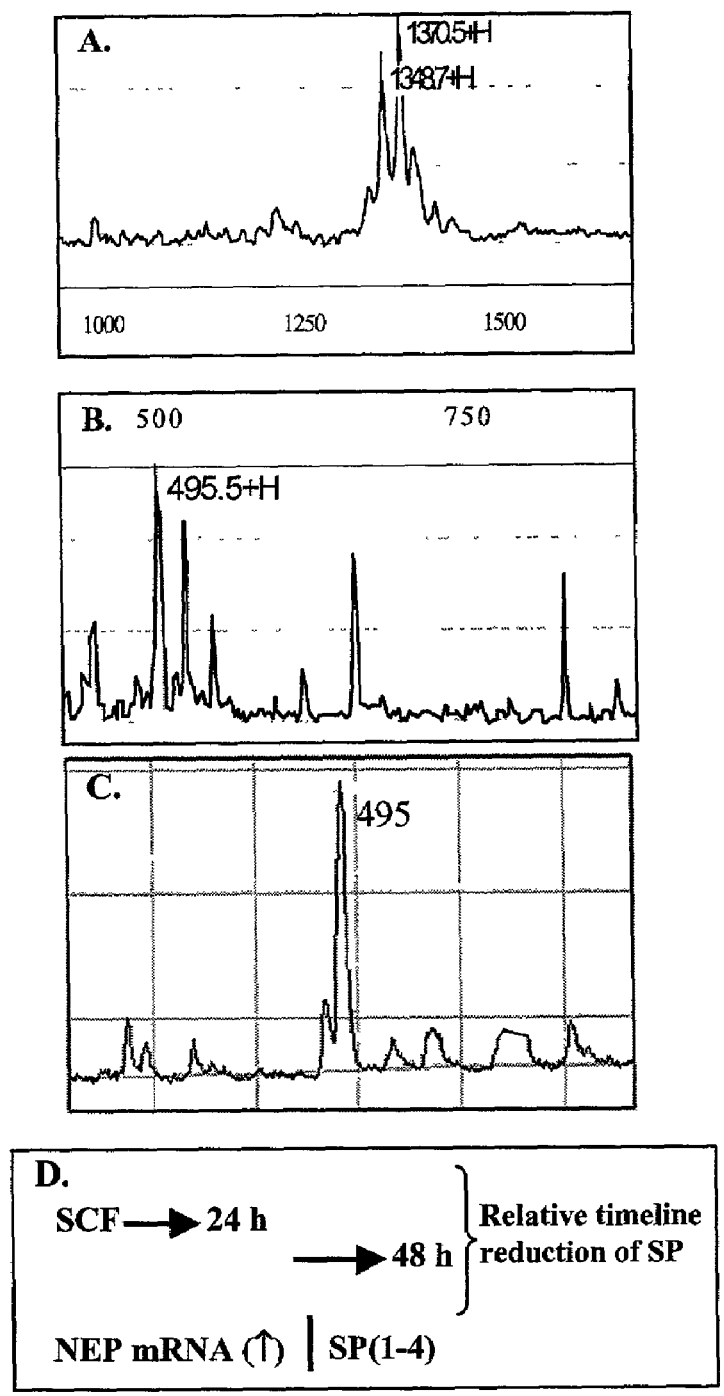
FIG. 5. Standard chromatogram for profiling studies for SP (A) or SP(1-4) (B) and for affinity detection of SP(1-4) (C). A scheme showing optimal level of SP at 24 h, which was reduced at 48 h. Between 16 and 24 h, NEP mRNA is induced, which is followed by the appearance of SP(1-4) at 48 h (D).

Further, the experimental evidence also suggested that SP(1-4) had negative hematopoietic effects that were later determined to be mediated through NK-1[8]. An understanding of the role of NK-1 in SP(1-4) effect was provided by the appearance of SP(1-4) in SCF-stimulated cells (FIG. 5) while NK-1 expression was still upregulated (FIG. 2, Table 2). SP was first detected in stromal cells stimulated with SCF. This was followed by the appearance of NEP and then the degradation of SP to SP(1-4) and later the induction, mediated by SP(1-4), of TGF-β and TNF-α (Table 1). Analyses of these results support the conclusion that the induction of NK-1 by SCF was blunted after the change of SP to SP(1-4) and with time, membrane expression of NK-1 was reduced (FIG. 2). The significance of this reduction is the provision of a feedback mechanism on the effects of SCF. Furthermore, the significance of the increased levels of TGF-β and TNF-α is that SP(1-4) can be used to stimulate TGF-β and TNF-α production and their resultant biological effects, namely the inhibition of stem cell proliferation and differentiation as well as the reduction of inflammation.

The present invention, therefore provides, generally, novel compositions that include SP(1-4) and NEP therapeutics that have been found to act as mediators of pluripotent stem or progenitor cell proliferation and/or its inhibition. Further, the present invention describes the use of such compositions for the protection of stem cells in a subject undergoing, or about to undergo, cancer related therapies.

In particular aspects, the invention relates to SP(1-4) compositions and methods for using such compositions for protecting stem and progenitor cells in a subject, undergoing or about to undergo a cancer related therapy such as chemo- and/or radio-therapy, by administering a SP(1-4) gene or protein, in a pharmaceutically acceptable and appropriate delivery vehicle. Specifically, in one aspect, the present invention relates to SP(1-4) polynucleotides and polypeptides. The SP(1-4) polypeptides include the polypeptide of SEQ ID NO:2; as well as polypeptides comprising the amino acid sequences which have at least 50% identity to that of SEQ ID NO:2, preferably 75% identity, and most preferably 100% identity to that of SEQ ID NO:2.

In a further aspect, the invention relates to NEP compositions and methods for using such compositions for protecting stem and progenitor cells in a subject, undergoing or about to undergo a cancer related therapy such as chemo- and/or radio-therapy, by administering a NEP gene or protein, in a pharmaceutically acceptable and appropriate delivery vehicle. Specifically, in one aspect, the present invention relates to NEP polynucleotides (described below) and proteins. The NEP proteins include the amino acid sequence of SEQ ID NO:4; as well as amino acid sequences that have at least 70% identity, preferably 80%, more preferably 90% or 95% and most preferably 100% sequence identity to that of SEQ ID NO:4.

Variants of the defined sequences and fragments, thereof, also form part of the present invention. As an example, preferred variants are those that vary from the referents by conservative amino acid substitutions. It is often advantageous to include an additional amino acid sequences which contain secretory or leader sequences, pro-sequences, sequences which aid in purification such as multiple histidine residues, or an additional sequence for stability during recombinant production. Preferably, the SP(1-4) polypeptide or NEP protein exhibits at least one biological activity of SP(1-4) or NEP, respectfully.

The SP(1-4) polypeptides or NEP proteins of the invention can be prepared in any suitable manner. More specifically, for NEP in particular, if produced in situ the protein may be purified from appropriate sources, e.g., appropriate vertebrate cells e.g., mammalian cells, for instance human. Alternatively, the availability of nucleic acid molecules encoding the proteins enables production of the proteins using in vitro expression methods known in the art. For example, a NEP cDNA or gene may be cloned into an appropriate in vitro transcription vector, for in vitro transcription, followed by cell-free translation in a suitable cell-free translation system. In vitro transcription and translation systems are commercially available, e.g., from Promega Biotech, Madison, Wis., or BRL, Rockville, Md. While in vitro transcription and translation is not the method of choice for preparing large quantities of the protein, it is ideal for preparing small amounts of native or mutant peptides for research purposes, particularly since it allows the incorporation of radioactive nucleotides.

For the preparation of larger quantities of the NEP protein (or even the SP(1-4) polypeptide), the protein may be produced by expression in a suitable prokaryotic or eukaryotic system. For example, part or all of a DNA molecule, such as the polynucleotide code which encodes the protein of SEQ ID NO:4, may be inserted into a plasmid vector adapted for expression in a bacterial cell (such as *E. coli*) or a yeast cell (such as *Saccharomyces cerevisiae*). Such vectors comprise the regulatory elements necessary for expression of the DNA in the host cell, positioned in such a manner as to permit expression of the DNA into the host cell. Such regulatory elements required for expression include promoter sequences, transcription initiation sequences and, optionally, enhancer and inducer sequences.

Secretion signals may be used to facilitate purification of the resulting protein. The coding sequence for the secretion peptide is operably linked to the 5' end of the coding sequence for the protein, and this hybrid nucleic acid molecule is inserted into a plasmid adapted to express the protein in the host cell of choice. Plasmids specifically designed to express and secrete foreign proteins are available from commercial sources. For example, if expression and secretion is desired in E. coli, commonly used plasmids include pTrcPPA (Pharmacia); pPROK-C and pKK233-2 (Clontech); and pNH8a, pNH16a, pcDNAII and pAX (Stratagene), among others.

The NEP protein (or SP(1-4) polypeptide) produced by in vitro transcription and translation or by gene expression in a recombinant procaryotic or eukaryotic system may be purified according to methods known in the art. Recombinant peptides can be purified by affinity separation, such as by immunological interaction with antibodies that bind specifically to the peptide or fusion proteins such as His tags, as described below. Such methods are commonly used by skilled practitioners.

As mentioned, the protein can be produced and fused to a "tag" protein in order to facilitate subsequent purification. These fusion proteins are produced by operably-linking the nucleic acid coding sequence of the "tag" protein to the coding sequence of the peptide of interest, and expressing the fused protein by standard methods. Systems are commercially available that comprise a plasmid containing an expression cassette with the "tag" protein coding sequence and a polylinker into which a coding sequence of interest can be operably ligated. These fusion protein systems further provide chromatography matrices or beads that specifically bind the "tag" protein thereby facilitating the fusion protein purification. These fusion protein systems often have the recognition sequence of a protease at or near the junction of the "tag" protein and the protein of interest so that the "tag" protein can be removed if desired. Fusion protein systems include, but are not limited to, the His-6-tag system (Quiagen) and the glutathione-S-transferase system (Pharmacia).

More specifically, with regard to the SP(1-4) polypeptide, using the appropriate amino acid sequence information, synthetic SP(1-4) polypeptides of the present invention may be prepared by various synthetic methods of peptide synthesis via condensation of one or more amino acid residues, in accordance with conventional peptide synthesis methods. Preferably, peptides are synthesized according to standard solid-phase methodologies, such as may be performed on an Applied Biosystems Model 430A peptide synthesizer (Applied Biosystems, Foster City, Calif.), according to manufacturer's instructions. Other methods of synthesizing peptides or peptidomimetics, either by solid phase methodologies or in liquid phase, are well known to those skilled in the art.

Polynucleotides

In a further embodiment of the present invention, compositions containing a NEP therapeutic are provided. In mammals, NEP is found in a variety of tissues, including kidney, lung, testes, brain and bone marrow as well as both stem and progenitor cell surface membranes. It is an integral membrane glycoprotein with a structure having a twenty amino acid cytoplasmic domain, a single twenty-three amino acid membrane spanning domain, and a 699 amino acid extra-cellular domain, which includes the active site of the enzyme. And although, NEP's biological function varies from tissue to tissue, NEP cleaves peptides on the amino side of hydrophobic amino acids. There are numerous physiologically active peptides that can be considered as potential in vivo substrates of the enzyme, however it is the most active peptidase which acts on substance P.

A NEP therapeutic may include an NEP genetic sequence such as a DNA, RNA, or antisense RNA polynucleotide sequence as well as antibodies immunospecific for NEP. The NEP polynucleotides of the present invention include isolated polynucleotides encoding the NEP protein, and polynucleotides closely related thereto. More specifically, NEP polynucleotides of the invention include a polynucleotide comprising the human nucleotide sequences contained in SEQ ID NO:3 encoding an NEP polypeptide of SEQ ID NO:4.

The compositions of the present invention may also include polynucleotide sequences that have at least 70% identity over its entire length to a nucleotide sequence encoding the NEP polypeptide of SEQ ID NO:4, so long as the sequence encodes an NEP protein capable of expression within the cell and capable of the catalytic cleavage of SP to SP(1-4). In this regard, polynucleotides with at least 70% are preferred, more preferably at least 80% even more preferably at least 90% identity, yet more preferably at least 95% identity, 97% are highly preferred and those with at least 98–99% are most highly preferred, with at least 99% being the most preferred. Also included under NEP polynucleotides are nucleotide sequences that have sufficient identity to a nucleotide sequence contained in SEQ ID NO:3, to hybridize under conditions useable for amplification and intracellular expression. The invention also provides polynucleotides that are complementary to such NEP polynucleotides. Thus, this invention provides oligonucleotides (sense or antisense strands of DNA, cDNA or RNA) having sequences capable of hybridizing with at least one sequence of a nucleic acid molecule encoding the protein of the present invention.

Further, a composition containing an SP(1-4) polynucleotide sequence is provided. The SP(1-4) polynucleotides, of the present invention, include the polynucleotide sequence of SEQ ID NO:1; as well as polynucleotide sequences that have at least 70% identity, preferably 80%, more preferably 90% or 95% and most preferably 100% sequence identity to that of SEQ ID NO:1.

NEP polynucleotides or SP(1-4) polynucleotides of the present invention may be prepared by at least two general methods: (1) they may be synthesized from appropriate nucleotide triphosphates, or (2) they may be isolated from biological sources. Both methods utilize protocols well known in the art. The availability of nucleotide sequence information, such as the cDNA having SEQ ID NO:1 or 3, enables preparation of an isolated nucleic acid molecule of the invention by oligonucleotide synthesis.

Synthetic oligonucleotides may be prepared by the phosphoramadite method employed in the Applied Biosystems 38A DNA Synthesizer or similar devices. The resultant construct may be purified according to methods known in the art, such as high performance liquid chromatography (HPLC). Long, double-stranded polynucleotides, must be synthesized in stages, due to the size limitations inherent in current oligonucleotide synthetic methods. Thus, for example, a long double-stranded molecule may be synthesized as several smaller segments of appropriate complementarity. Complementary segments thus produced may be annealed such that each segment possesses appropriate cohesive termini for attachment of an adjacent segment. Adjacent segments may be ligated by annealing cohesive termini in the presence of DNA ligase to construct an entire long double-stranded molecule. A synthetic DNA molecule so constructed may then be cloned and amplified in an appropriate vector.

In accordance with the present invention, nucleic acids having the appropriate level sequence homology (i.e., 70% identity or greater) with part or all the coding regions of SEQ ID NO:3 may be identified by using hybridization and washing conditions of appropriate stringency. For example, hybridizations may be performed, according to the method of Sambrook et al., using a hybridization solution comprising: 1.0% SDS, up to 50% formamide, 5×SSC (150 mM NaCl, 15 mM trisodium citrate), 0.05% sodium pyrophosphate (pH 7.6), 5× Denhardt's solution, and 100 microgram/ml denatured, sheared salmon sperm DNA. Hybridization is carried out at 37–42° C. for at least six hours. Following hybridization, filters are washed as follows: (1) 5 minutes at room temperature in 2×SSC and 1% SDS; (2) 15 minutes at room temperature in 2×SSC and 0.1% SDS; (3) 30 minutes to 1 hour at 37° C. in 2×SSC and 0.1% SDS; (4) 2 hours at 45–55° C. in 2×SSC and 0.1% SDS, changing the solution every 30 minutes.

Vectors, Host Cells, and Expression

The present invention also relates to vectors that include a polynucleotide or polynucleotides of the present invention, and to the production of polypeptides of the invention by recombinant techniques both in vitro and in vivo, as well as ex vivo procedures. Cell-free translation systems can also be employed to produce such proteins using RNAs derived from the DNA constructs of the present invention.

For recombinant production, host cells can be genetically engineered to incorporate expression systems or portions thereof for polynucleotides of the present invention. In accordance with the methods of the present invention, host cells may also be obtained from the BM of a subject by procedures well known in the medical arts. Introduction of polynucleotides into host cells can then be effected by methods described in many standard laboratory manuals, such as Davis et al., Basic Methods In Molecular Biology (1986) and Sambrook et al., Molecular Cloning: A Laboratory Manual, 2nd Ed., Cold Spring Harbor Laboratory Press, Cold Spring Harbor, N.Y. (1989) such as calcium phosphate transfection, DEAE-dextran mediated transfection, microinjection, cationic lipid-mediated transfection, electroporation, transduction, scrape loading, ballistic introduction or infection.

Representative examples of appropriate hosts for in vitro procedures include bacterial cells, such as *Streptococci, Staphylococci, E. coli, Streptomyces* and *Bacillus subtilis* cells; fungal cells, such as yeast cells and *Aspergiffits* cells; insect cells such as *Drosophila* S2 and *Spodoptera* Sf9 cells; animal cells such as CHO, COS, HeLa, C127, 3T3, BHK, HEK 293 and Bowes melanoma cells, and plant cells. The selection of an appropriate host is deemed to be within the scope of those skilled in the art from the teachings herein.

More particularly, the present invention also includes recombinant constructs, such as expression cassettes, comprising a NEP therapeutic selected from the group including DNA, cDNA or RNA sequence, anti-sense RNA sequence, as well as compliment nucleotide sequences for triplexing duplex DNA. The construct comprises a vector, such as a plasmid or viral vector, into which the clone has been inserted, in a forward or reverse orientation. In a preferred aspect of this embodiment, the construct further comprises regulatory sequences, including, for example, a promoter, operably linked to the genetic sequence. Large numbers of suitable vectors and promoters are known to those of skill in the art, and are commercially available. The following vectors are provided by way of example; Bacterial: pQE70, pQE60, pQE-9 (Qiagen), pBS, pD10, phagescript, psiX 174, pbluescript SK, pbsks, pNH8A, pNH 16a, pNHI8A, pNH46A (Stratagene); ptrc99a, pKK223-3, pKK233-3, pDR540, pRIT5 (Pharmacia); Eukaryotic: pWLNEO, pSV2CAT, pOG44, pXTI, pSG (Stratagene) pSVK3, pBPV, pMSG, pSVL (Pharmacia). As further examples, cDNA of human NEP may be inserted in the pEF/myc/cyto vector (from Invitrogen) and/or the pCMV-Tag3b vector (from Stratagene), which can then be used with anti-Myc Ab, to transform Stem or HeLa (or other) cells with the NEP DNA. However, any other plasmid or vector may be used as long as they are replicable and viable in the host.

In addition, a complete mammalian transcription unit and a selectable marker can be inserted into a prokaryotic plasmid for use in in vivo procedures. The resulting vector is then amplified in bacteria before being transfected into cultured mammalian cells or delivered directly to the subject with an acceptable biological carrier as described below. Examples of vectors of this type include pTK2, pHyg and pRSVneo. Hence, these plasmids, constructs and vectors may be used in both in vivo and ex vivo procedures. Ex vivo procedures involve the removal of a host cell, such as a BM, stromal or stem cell, from the subject, recombinant manipulation of the cell (i.e., transformation, transduction or transfection with a suitable NEP expression system vector), and the re-delivery of the cell back into its host environment.

A wide variety of recombinant plasmids may be engineered to express the NEP protein and used for delivery of an NEP therapeutic to a cell. These include the use of naked DNA and NEP plasmids to directly transfer genetic material into a cell (Wolfe et al., 1990); formulations of NEP encoding trapped liposomes (Ledley et. al., 1987) or in proteoliposomes that contain other viral envelope receptor proteins (Nicolau et al., 1983); and NEP-encoding DNA, or antisense sequence, coupled to a polysineglycoprotein carrier complex. Further, recombinant NEP DNA, cDNA, RNA, or polynucleotide sequence coding for the antisense sequence encoding the protein, may be directly injected into the BM for the production or inhibition of NEP endogenously. Hence methods for the delivery of nucleotide sequences to cells are well known in the recombinant arts. Other methods for in vitro delivery include, but are not limited to: microinjection, calcium phosphatase, lyposomes, and electroporation. NEP DNA, cDNA, RNA or polynucleotide sequences coding for the antisense sequence encoding the protein may also be delivered using other appropriate means, including vectors, as described below, and well known in the recombinant arts.

Genetic material, such as the nucleotides of the present invention, may be delivered to cells, in vivo, using various different plasmid based delivery platforms, including but not limited to recombinant ADV (such as that described in U.S. Pat. No. 6,069,134 incorporated by reference herein), AAV (such as those described by U.S. Pat. No. 5,139,941 incorporated by reference herein), MMLV, Herpes Simplex Virus (U.S. Pat. No. 5,288,641, incorporated by reference herein), cytomegalovirus, lentiviral, and overall, retroviral gene delivery systems, well known and practiced with in the art.

Techniques for preparing replication defective, infective viruses are well known in the art, as exemplified by Ghosh-Choudhury & Graham (1987); McGory et al., (1988); and Gluzman et al., (1982), each incorporated by reference herein. These systems typically include a plasmid vector including a promoter sequence (such as CMV early promoter) operably linked to the nucleotide coding the gene of interest (inserted into an appropriate gene insertion site; i.e., an IRES site), as well as a terminating signal (such as a Poly-A tail i.e., BGH), and the appropriate mutations so as to make the delivery vehicle replication defective (e.g., Psi sequence deletions) and safe for therapeutic uses. The construction of the appropriate elements in a vector system containing the nucleotides of the present invention is well within the skills of one versed in the recombinant arts.

A great variety of vector and/or expression systems can be used. Such systems include, among others, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia, viruses, adenoviruses, fowl pox viruses, pseudorabies viruses and retroviruses, and vectors derived from combinations thereof, such as those derived from plasmid and bacteriophage genetic elements, such as cosmids and phagemids. The expression systems may contain control regions that regulate as well as engender expression. Generally, any system or vector suitable to maintain, propagate or express polynucleotides to produce a polypeptide in a host may be used. The appropriate nucleotide sequence may be inserted into an expression system by any of a variety of well-known and routine techniques, such as, for example, those set forth in Sambrook et al., *Molecular Cloning, A Laboratory Manual* (supra).

Promoter regions can be selected from any desired gene using CAT (chloramphenicol acetyl transferase) vectors or other vectors with selectable markers. Two appropriate vectors are pKK232-8 and pCM7. Particular named bacterial promoters include lacI, lacZ, T3, T7, gpt, lambda PR, PL and trp. Eukaryotic promoters include CMV immediate early, HSV thymidine kinase, early and late SV40, LTRs from retrovirus, and mouse metallothionein-1. Selection of the appropriate vector and promoter is well within the level of ordinary skill in the art.

The above-described constructs, plasmids and vectors are useful in supplying NEP genetic elements to host cells. A successful procedure generally requires the integration of the gene coding for the NEP protein into the host genome, where it would co-exist and replicate with the host DNA and be expressed at an increased level. There are several approaches to NEP gene delivery in this regard.

As described above, basic transfection methods exist in which DNA containing the gene of interest is introduced into cells non-biologically, for example, by permeabilizing the cell membrane physically or chemically. Liposomes or protein conjugates formed with certain lipids and amphophilic peptides can be used for transfection. (Stewart et al., 1992; Torchilin et al., 1992; Zhu et al., 1993, incorporated herein by reference.) This approach is particularly effective in ex vivo procedures involving leukocytes, which can be temporarily removed from the body and can tolerate the cytotoxicity of the treatment.

A second, transduction approach, capitalizes on the natural ability of viruses to enter cells, bringing their own genetic material with them. For example, retroviruses have promise as gene delivery vectors due to their ability to integrate their genes into the host genome, transferring a large amount of foreign genetic material, infecting a broad spectrum of species and cell types and of being packaged in special cell-lines (Miller, 1992, incorporated herein by reference).

A third method uses other viruses, such as adenovirus, herpes simplex viruses (HSV), cytomegalovirus (CMV), and adeno-associated virus (AAV), which are engineered to serve as vectors for gene transfer. Although some viruses that can accept foreign genetic material are limited in the number of nucleotides they can accommodate and in the range of cells they infect, these viruses have been demonstrated to successfully effect gene expression. For example, adenovirus gene transfer systems may be used. Such a system is based upon recombinant, engineered adenovirus which is rendered replication-incompetent by deletion of a portion of its genome, such as E1, and yet still retains its competency for infection. Relatively large foreign proteins can be expressed when additional deletions are made in the adenovirus genome. For example, adenoviruses deleted in both E1 and E3 regions are capable of carrying up to 10 Kb of foreign DNA and can be grown to high titers in 293 cells (Stratford-Perricaudet and Perricaudet, 1991a). Surprisingly persistent expression of transgenes following adenoviral infection has also been reported.

Further still, the recombinant NEP DNA, cDNA, RNA or polynucleotide sequences coding for the antisense sequence encoding the protein as well as antibodies immunospecific NGI, may be delivered to the cells of the BM for the production or inhibition of NEP endogenously, by use of biologically compatible carriers or excipients. This may be useful in inducing or inhibiting stem cell proliferation and/or possibly differentiation. Pharmaceutically acceptable carriers for therapeutic use are well known in the pharmaceutical art, and are described, for example, in Remington's Pharmaceutical Sciences (A. P. Gennaro, ed.; Mack, 1985). For example, sterile saline or phosphate-buffered saline at physiological pH may be used. Preservatives, stabilizers, dyes, and even flavoring agents may be provided in the pharmaceutical composition. For example, sodium benzoate, sorbic acid, and esters of p-hydroxybenzoic acid may be added as preservatives. Antioxidants and suspending agents may also be used.

The pharmaceutical compositions of the present invention may be formulated and used as tablets, capsules, or elixirs for oral administration; suppositories for rectal or vaginal administration; sterile solutions and suspensions for parenteral administration; creams, lotions, or gels for topical administration; aerosols or insufflations for intratracheobronchial administration; and the like. Preparations of such formulations are well known to those skilled in the pharmaceutical arts. The dosage and method of administration can be tailored to achieve optimal efficacy and will depend on factors that those skilled in the medical arts will recognize.

When administration is to be parenteral, such as intravenous on a daily basis, injectable pharmaceuticals may be prepared in conventional forms, either as liquid solutions or suspensions; solid forms suitable for solution or suspension in liquid prior to injection; or as emulsions. Suitable excipients are, for example, water, saline, dextrose, mannitol, lactose, lecithin, albumin, sodium glutamate, cysteine hydrochloride, or the like. In addition, if desired, the injectable pharmaceutical compositions may contain minor amounts of nontoxic auxiliary substances, such as wetting agents, pH buffering agents, and the like. If desired, absorption enhancing preparations (e.g. liposomes) may be utilized.

Hence, a preferred embodiment the present invention is directed to novel pharmaceutical compositions that include a biologically acceptable carrier along with an effective amount of a SP(1-4) polypeptide, NEP protein, SP(1-4) or NEP DNA, cDNA or RNA for the protection of stem and progenitor cells in those undergoing, or about to undergo, chemo-and/or radio-therapy.

In one particular embodiment the pharmaceutical composition includes an SP(1-4) polypeptide sequence substantially identical to SEQ ID No:2 and/or the polynucleotide sequence that is substantially similar to SEQ ID NO:1 and encodes an SP(1-4) polypeptide. In a further embodiment, the pharmaceutical composition includes a NEP polynucleotide sequence substantially identical to SEQ ID NO:3 and/or a protein encoded by an amino acid sequence substantially identical to the sequence of SEQ ID NO:4. Also provided are methods for the pretreatment of those suffering from diseases where by the administration of chemo-and/or radiotherapy is an option. Pretreatment with the above described compositions may be useful in protecting stem and progenitor cells from the toxic effects of chemo-radiotherapy. These methods involve administering to the subject a pharmaceutical composition that includes an effective amount of a SP(1-4) or NEP protein or a nucleotide sequence coding for the SP(1-4) or NEP protein. These may be delivered by suitable means, as described above, including the use of vectors and or acceptable biological carriers, to a subject's stem and/or progenitor cells, which cells may include lymphoid, myeloid, LTC-IC, CFU-GM, CFU-E, CFU-B, burst-forming unit-erythroid, colony forming unit-erythroid and colony forming unit-megakaryocyte cells.

For the treatment of and/or prevention of diseases associated with the post operative condition, where an increase in stem or progenitor cell proliferation is desired, a pharmaceutical composition that includes an effective amount of a NEP nucleotide sequence coding for the antisense sequence of SEQ ID NO:3, or an antibody, immunospecific for the NEP protein, may be administered. An example of such a diseased state that may be treated by the compositions of the present invention are fungal and/or bacterial related infections that may result from undergoing chemo-radiotherapy for the treatment of leukemia and lymphoma Antibodies The present invention also provides antibodies capable of immunospecifically binding to NEP proteins of the invention. Polyclonal or monoclonal antibodies directed towards the protein encoded by NEP may be prepared according to standard methods. Monoclonal antibodies may be prepared according to general hybridoma methods of Kohler and Milstein, *Nature* (1975) 256:495–497), the trioma technique, the human B-cell hybridoma technique (Kozbor et al., *Immunology Today* (1983) 4:72) and the EBV-hybridoma technique (Cole et al., *Monoclonal Antibodies And Cancer Therapy*, pp. 77–96, Alan R. Liss, Inc., 1985).

Antibodies utilized in the present invention may be polyclonal antibodies, although monoclonal antibodies are preferred because they may be reproduced by cell culture or recombinantly, and may be modified to reduce their antigenicity.

Polyclonal antibodies may be raised by a standard protocol by injecting a production animal with an antigenic composition, formulated as described above. See, e.g., Harlow and Lane, Antibodies: A Laboratory Manual, Cold Spring Harbor Laboratory, 1988. In one such technique, a NEP antigen comprising an antigenic portion of the NEP protein is initially injected into any of a wide variety of mammals (e.g., mice, rats, rabbits, sheep or goats). Alternatively, in order to generate antibodies to relatively short peptide portions NEP, a superior immune response may be elicited if the polypeptide is joined to a carrier protein, such as ovalbumin, BSA or KLH. The peptide-conjugate is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Alternatively, for monoclonal antibodies, hybridomas may be formed by isolating the stimulated immune cells, such as those from the spleen of the inoculated animal. These cells are then fused to immortalized cells, such as myeloma cells or transformed cells, which are capable of replicating indefinitely in cell culture, thereby producing an immortal, immunoglobulin-secreting cell line. The immortal cell line utilized is preferably selected to be deficient in enzymes necessary for the utilization of certain nutrients. Many such cell lines (such as myelomas) are known to those skilled in the art, and include, for example: thymidine kinase (TK) or hypoxanthine-guanine phosphoriboxyl transferase (HGPRT). These deficiencies allow selection for fused cells according to their ability to grow on, for example, hypoxanthine aminopterinthymidine medium (HAT).

Preferably, the immortal fusion partners utilized are derived from a line that does not secrete immunoglobulin. The resulting fused cells, or hybridomas, are cultured under conditions that allow for the survival of fused, but not unfused, cells and the resulting colonies screened for the production of the desired monoclonal antibodies. Colonies producing such antibodies are cloned, expanded, and grown so as to produce large quantities of antibody, see Kohler and Milstein, 1975 Nature 256:495 (the disclosures of which are hereby incorporated by reference).

Large quantities of monoclonal antibodies from the secreting hybridomas may then be produced by injecting the clones into the peritoneal cavity of mice and harvesting the ascites fluid therefrom. The mice, preferably primed with pristine, or some other tumor-promoter, and immunosuppressed chemically or by irradiation, may be any of various suitable strains known to those in the art. The ascites fluid is harvested from the mice and the monoclonal antibody purified therefrom, for example, by CM Sepharose column or other chromatographic means. Alternatively, the hybridomas may be cultured in vitro or as suspension cultures. Batch, continuous culture, or other suitable culture processes may be utilized. Monoclonal antibodies are then recovered from the culture medium or supernatant.

In addition, the antibodies or antigen binding fragments may be produced by genetic engineering. In this technique, as with the standard hybridoma procedure, antibody-producing cells are sensitized to the desired antigen or immunogen. The messenger RNA isolated from the immune spleen cells or hybridomas is used as a template to make cDNA using PCR amplification. A library of vectors, each containing one heavy chain gene and one light chain gene retaining the initial antigen specificity, is produced by insertion of appropriate sections of the amplified immunoglobulin cDNA into the expression vectors. A combinatorial library is constructed by combining the heavy chain gene library with the light chain gene library. This results in a library of clones that co-express a heavy and light chain (resembling the Fab fragment or antigen binding fragment of an antibody molecule). The vectors that carry these genes are co-transfected into a host (e.g. bacteria, insect cells, mammalian cells, or other suitable protein production host cell.). When antibody gene synthesis is induced in the transfected host, the heavy and light chain proteins self-assemble to produce active antibodies that can be detected by screening with the antigen or immunogen.

Chimeric antibodies may be made by recombinant means by combining the murine variable light and heavy chain regions (VK and VH), obtained from a murine (or other animal-derived) hybridoma clone, with the human constant light and heavy chain regions, in order to produce an antibody with predominantly human domains. The production of such chimeric antibodies is well known in the art, and may be achieved by standard means (as described, e.g., in U.S. Pat. No. 5,624,659, incorporated fully herein by reference). Humanized antibodies are engineered to contain even more human-like immunoglobulin domains, and incorporate only the complementarity-determining regions of the animal-derived antibody. This is accomplished by carefully examining the sequence of the hyper-variable loops of the variable regions of the monoclonal antibody, and fitting them to the structure of the human antibody chains. Although facially complex, the process is straightforward in practice. See, e.g., U.S. Pat. No. 6,187,287, incorporated fully herein by reference.

In a preferred embodiment, antibodies are prepared, which react immunospecifically with various epitopes of the NEP encoded protein. These above-described antibodies may be employed to bind to the endogenous NEP protein on a cell's surface membrane and thereby prevent it from binding to and degrading SP. Hence, these antibodies may be used in pharmaceutical compositions for therapeutic purposes where it is desirable to promote stem cell proliferation, such as in a post chemo-radio-therapeutic condition to help prevent fungal and/or bacterial infection and to speed recovery. Specific antibodies may be made in vivo using recombinant DNA and methods well know in the art.

For administration, the antibody-therapeutic agent will generally be mixed, prior to administration, with a nontoxic, pharmaceutically acceptable carrier substance. Usually, this will be an aqueous solution, such as normal saline or phosphate-buffered saline (PBS), Ringer's solution, lactate-Ringer's solution, or any isotonic physiologically acceptable solution for administration by the chosen means. Preferably, the solution is sterile and pyrogen-free, and is manufactured and packaged under current Good Manufacturing Processes (GMP's), as approved by the FDA. The clinician of ordinary skill is familiar with appropriate ranges for pH, tonicity, and additives or preservatives when formulating pharmaceutical compositions for administration by intravascular injection, intrathecal injection, injection into the BM, direct injection into the aberrant cell, or by other routes. In addition to additives for adjusting pH or tonicity, the antibody-therapeutics agent may be stabilized against aggregation and polymerization with amino acids and non-ionic detergents, polysorbate, and polyethylene glycol.

Optionally, additional stabilizers may include various physiologically-acceptable carbohydrates and salts. Also, polyvinylpyrrolidone may be added in addition to the amino acid. Suitable therapeutic immunoglobulin solutions, which are stabilized for storage and administration to humans, are described in U.S. Pat. No. 5,945,098, incorporated fully herein by reference. Other agents, such as human serum albumin (HSA), may be added to the therapeutic composition to stabilize the antibody conjugates. The compositions of the invention may be administered using any medically appropriate procedure, e.g., intravascular (intravenous, intraarterial, intracapillary) administration, injection into the BM, intracavity or direct injection in the stem cell. Intravascular injection may be by intravenous or intraarterial injection.

The effective amount of the therapeutic antibody composition to be given to a particular patient will depend on a variety of factors, several of which will be different from patient to patient. A competent clinician will be able to determine an effective amount of a therapeutic antibody-conjugate composition to administer to a patient to retard the growth and promote the death of leukemia/lymphoma associated cells. Dosage of the antibody-therapeutic will depend on the type of treatment previously administered, route of administration, the nature of the therapeutics, sensitivity of the stem cells to the therapeutics, etc. Utilizing $LD_{50}$ animal data, and other information available, a clinician can determine the maximum safe dose for an individual, depending on the route of administration. For instance, an intravenously administered dose may be more than an intrathecally administered dose, given the greater body of fluid into which the therapeutic composition is being administered. Similarly, compositions, which are rapidly cleared from the body, may be administered at higher doses, or in repeated doses, in order to maintain a therapeutic concentration. Utilizing ordinary skill, the competent clinician will be able to optimize the dosage of a particular therapeutic composition in the course of routine clinical trials.

The foregoing is intended to be illustrative of the embodiments of the present invention, and are not intended to limit the invention in any way. Although the invention has been described with respect to specific modifications, the details thereof are not to be construed as limitations, for it will be apparent that various equivalents, changes and modifications may be resorted to without departing from the spirit and scope thereof and it is understood that such equivalent embodiments are to be included herein. All publications and patent applications are herein incorporated by reference to the same extent as if each individual publication or patent application was specifically and individually indicated to be incorporated by reference.

EXAMPLES

The following description sets forth the general procedures involved in practicing the present invention. To the extent that specific materials are mentioned, it is merely for purposes of illustration and is not intended to limit the invention. Unless other-wise specified, general cloning procedures, such as those set forth in Sambrook et al., *Molecular Cloning*, supra or Ausubel et al., (eds) *Current Protocols in Molecular Biology*, John Wiley & Sons (2000) (hereinafter "Ausubel et al.") are used. See the examples below for further details.

EXAMPLE I

A. Reagents, Cytokines and Antibodies

SP, SP(1-4), thiazolyl blue (MTT), spantide, Ficoll-Hypaque and non-immune rabbit serum were purchased from Sigma (St. Louis, Mo.). Spantide, SP and SP(1-4) were dissolved and stored as described[22]. Biotin-SP and biotin-NK-A were purchased from Peninsula Laboratories (Belmont, Calif.). Alkaline phosphatase (Alk Phos)—conjugated goat anti-rabbit IgG was obtained from Kirkegaard & Perry Laboratories Inc. (Gaithersburg, Md.). Rabbit anti-SP was purchased from Biogenesis (Brentwood, N.H.). The Immunology Department of Genetics Institute (Cambridge, Mass.) provided recombinant human (rh) GM-CSF. FITC-avidin was purchased from Vector Laboratories (Burlingame, Calif.). SCF, TGF-β1, TNF-α, goat anti-hTNF-α, rabbit anti-hTGF-13, biotinylated goat anti-hSCF receptor (c-kit), non-immune rabbit IgG, and biotinylated non-immune goat IgG were purchased from R&D Systems (Minneapolis, Minn.). Functional studies indicated that anti-hTGF-β exerts specificity by neutralizing the β1 form of TGF proteins[23].

B. Clonogenic Assays for CFU-GM

BM aspirate was obtained from the posterior iliac crest of normal healthy volunteers. Mononuclear cells were isolated by Ficoll-Hypaque density gradient and then assayed for CFU-GM in sera-free cultures as described[3]. Briefly, $10^5$ BM mononuclear cells/ml were plated in methylcellulose with 10 or 1 nM of SP(1-4). Each experimental point was assayed in duplicate. Cultures were assayed in parallel in the presence or absence of anti-TGF-β or anti-TNF-α, each ranging between 2 μg/ml and 10 ng/ml. Cultures contained 3 U/ml of rhGM-CSF. At day 10, the number of colonies with >20 cells were counted. Control cultures, which media alone or non-immune IgG showed similar numbers of CFU-GM ranging between 155 and 80.

C. Modified Long Term Culture-Initiating Cell (LTC-IC)

Confluent stromal cells were cultured in 25 cm$^2$ flasks and then subjected to 150 Gy, delivered by a cesium source. BMNC, $10^7$, were added to the flask containing the γ-irradiated stroma. Beginning at wk 5 of culture, aliquots of cells were assayed for CFU-GM every week up to 12 weeks.

D. Preparation and Stimulation of BM Stroma

Stromal cultures were prepared with BM aspirates from healthy donors as described[24]. Briefly, stromal cells were cultured at 33° C. and at day 3, the granulocytes and red blood cells were removed by Ficoll-Hypaque density gradient. Cultures were reincubated with weekly replacement of 50% culture media until confluence. Cytokine, NK receptor and c-kit expressions were studied in confluent stroma, stimulated with 10 nM SP(1-4) and/or 10 ng/ml SCF. Stroma was stimulated in 3 ml sera-free cc-MEM, supplemented with insulin-transferring-selenium-A (Life Technologies, Grand Island, N.Y.). At 16 h, stromal monolayers were washed with sera-free α-MEM and then re-incubated for 16 h with media, 10 nM SP(1-4) or 10 ng/ml SCF. Controls included stroma cultured for 16 h or 32 h in media alone. Time-course and dose-response curves established the optimal concentrations of SCF and SP(1-4).

The relative expression of c-kit in BM stroma was determined by immunofluorescence. BM stroma was cultured on coverslips (Fisher Scientific, Springfield, N.J.) and then stimulated with 10 ng/ml of SCF. At different times after cell stimulation, cells were labeled with 50 ng/ml of biotinylated goat anti-c-kit and FITC-avidin. Non-specific binding was determined with biotinylated non-immune goat anti-IgG. Cells were immediately examined on an OlympusProbis microscope (New York/New Jersey Scientific, Inc., Middlebush, N.J.). The fluorescence intensity at excitation of 595 nm was dim in unstimulated stroma and increased to bright in cells stimulated for 6 h to 24 h.

E. Quantitation of SP-Immunoreactivity (SP-IR)

Competitive ELISA quantitated SP-IR as described[3]. Briefly, Immulon 96-well plates (Dynatech Laboratories Inc., Chantilly, Va.) were precoated with streptavidin and then incubated with biotinylated SP (Chiron Mimotopes, Emeryville, Calif.). Equal volumes (50 μl) of unknown samples and optimum rabbit anti-SP were added to quadruplicate wells. Each sample was assayed as undiluted and three serial dilutions. Complexed anti-SP was detected with Alk Phos-conjugated goat anti-rabbit IgG and Sigma 104 phosphatase substrate. SP-IR levels were calculated from a standard curve developed with O.D. at 405 nm vs. 12 serial dilutions of known SP concentrations, ranging from 100 to 0.08 pg/ml.

F. Quantitative RT-PCR

Quantitative RT-PCR for NK-1, NK-2 and β-PPT-I mRNA was performed as described[3, 24]. Briefly, 2 μg of total RNA from BM stroma was reverse transcribed and 200 ng cDNA used in PCR reactions with standard DNA at $\log_{10}$ fold dilutions ranging between $10^{-2}$ and $10^{-6}$ attomole/L. PCR products (10 μl) were separated on agarose containing ethidium bromide. The DNA was scanned with a Fluorimager (Molecular Dynamics, Sunnyvale, Calif.) and the densities analyzed with ImageQuant software (Molecular Dynamics, version 5.2). A standard curve was established for each unknown sample: Band densities of unknown/standard DNA vs. $\text{Log}_{10}$ standard DNA concentration. The concentration of the unknown sample was read at the point where the ratio of the unknown and standard were equivalent. Construction of DNA standards was previously described[24].

1. Immunofluorescence for NK Receptors

BM stroma was stimulated with 10 ng/ml of SCF. At 24 h, cells were washed and then immediately incubated at 4° C. for 2 h with 200 ng/ml of biotin-SP or biotin-NK-A. After this, cells were labeled with FITC-avidin for 30 min and then examined for fluorescence intensity with an Olympus Provis AX-70 at 480±40 nm/excitation and 535±50 nm/emission. Minimal fluorescence was observed in cells co-labeled with excess unconjugated SP or NK-A, or cells labeled with FITC-avidin alone. The optimal experimental conditions were determined in dose-response and time-course studies. Specificity of binding by SP or NK-A was studied in competition labeling with the pan-tachykinin antagonist, spantide.

2. TNF-α determination

L929 fibroblasts, $1.5 \times 10^4$ in 0.1 ml were seeded in 96-well flat-bottomed plates and then incubated at 37° C. At 16 h, 4 μg/ml of actinomycin D was added to wells. Unknown samples, each with four serial dilutions in 50 μL were added to triplicate wells. A standard curve was established in parallel with twelve serial dilutions of TNF-α beginning at 1.5 nM. Plates were incubated overnight and the next day, cell viability was determined using the MTT assay. Briefly 20 μL of MTT at 5 mg/ml was added to each well. The plates were incubated for 2 h at 37° C. and then centrifuged at 800 rpm for 5 min. Supernatants were removed and cells washed once with PBS by centrifugation at 2000 rpm for 5 min. Thiazolyl blue crystals were dissolved with 100 μl of isopropanol and the O.D. determined at 570–650 nm with a Kinectic microplate reader (Molecular Devices, Menlo Park, Calif.).

G. TGF-β Quantitation

Growth inhibition of CCL 64 cells forms the basis of the bioassay used to quantitate active TGF-β[25]. Each sample was tested in triplicate with 25 ml, 50 ml or 100 ml of supernatants. TGF-β levels were determined from a standard curve established with TGF-β concentrations ranging from 0.001 to 10 ng/ml vs. cell concentration. The presence of TGF-β1 was verified by reanalyses of samples containing >20 ng/ml TGF-β with neutralizing anti-hTGF-β1[25]. Neutralization was determined if the anti-TGF-β1 reversed the growth inhibitory effect of the supernatants.

1. Biopanning of Phage Display Library and Selection of Clones

Peptide binding sites were determined by screening a random dodecapeptide library, FliTrx, as per manufacturer's instruction (Invitrogen Co., Carlsbad, Calif.). Briefly, bacteria were induced with tryptophan and then passaged for 6 h in 60 mm petri dishes (Nunclon Delta, Nalge Nunc) that were pre-coated with 20 μg of SP(1-4). After the 7$^{th}$ passage, the adherent bacteria were expanded in liquid culture and then sub-cultured on agar. Forty colonies were expanded and the pellet from each bacterial culture was boiled in sample buffer and then spotted on methanol-soaked PVDF transfer membranes (NEN, Boston, Mass.). The membranes were consecutively incubated with 10 µg/ml of SP(1-4) overnight at room temperature and rabbit anti-SP for 2 h. Anti-SP was detected with Alk Phos-conjugated goat anti-rabbit IgG followed by incubation for 15 min with 5-bromo-4-chloro-3-indolyl-phosphatase/nitroblue tetrazolium phosphate substrate system (Kirkegaard and Perry Laboratories, Gaithersburg, Md.). A single blinded observer scored the relative intensities of the spots with zero for no detection and 4 for the highest intensity. Twenty clones with assignments between 1 and 4 were selected and further analyzed in Western blots using gradient gels of 4–20% (Invitrogen)[25]. Seven clones were finally selected based on the development of a single, dense band at the predicted $M_r$.

DNA was extracted from each clone (described above) and then sequenced in both orientations at the Molecular Core Facility, UMDNJ-New Jersey Medical School. DNA sequencing was performed with the FliTrx Forward and Rsr Reverse primers, provided with the Peptide library. Each clone was analyzed with the Wisconsin Genetics Computer Group (GCG) package of DNA/protein sequence analysis programs (version 10, Genetics Computer Group, Madison Wis.). Six clones were selected based on >40% identity to the protein sequence of NK-1[26].

2. Computer Modeling of SP and NK-1

The transmembrane (TM) portion of NK-1 was modeled using WHAT-IF® in conjunction with Swiss-Mod at the SIB and EMBL. The structures of both SP and NK-1 were generated using SYBYL 6.6 (TRIPOS Associates, St Louis, Mo.). A homologue of the TM region of NK-1 was modeled at the EMBL and Swiss-Model repository using WHAT-IF, an algorithm that maps the sequence onto a template structure. WHAT-IF optimizes the structure while adjusting for side-chain collisions and interactions. The template used was the alpha-carbon chain from the crystallized structure of the G-protein coupled receptor, bacteriorhodopsin[27]. The arrangement of the TM helices in bacteriorhodopsin is the conventional model for all members of the G-protein coupled receptor. The intracellular and extracellular loops were constructed using a loop search. SP was constructed ab-initio based on its sequence. A molecular dynamics run was performed using a timestep of 5, carried out through 500 iterations. Energy minimization was performed. Docking of SP into NK-1 was performed with SYBYL's Docking engine and Flexidock. All energetic calculations were performed using Kollman-United charges with the Tripos force field engine.

H. Northern Analyses

Northern analyses for steady state NEP and NK-1 mRNA were performed as described[28]. For NEP mRNA, stromal cells were stimulated with SCF for 16 h in sera-free α-MEM supplemented with Insulin-Transferring-Selenium-A. At different times after, total RNA was extracted and 10 µg used for northern analyses. Membranes were consecutively hybridized with [α-$^{32}$P]-dATP-labeled cDNA probes for NEP and 18S rRNA as described[3]. NK-1 mRNA was determined with total RNA from stromal cultures that were sequentially stimulated with SCF and SP(1-4), described above. The cDNA for NK-1 is previously described[29]. NK-2 cDNA was prepared by RT-PCR with total RNA from BM stroma as template and the same primers used for quantitative RT-PCR (described above). The NK-2 fragment, which was equivalent to 274 bp was subcloned into pNoTA/T7 (5 Prime→3 Prime, Boulder, Colo.). The cDNA for human NEP sand 18S rRNA were purchased from American Type Culture Collection (Manassas, Va.).

EXAMPLE II

A. Profiling for SP and SP(1-4) by ProteinChip Analyses

SP and SP(1-4) were profiled in stromal cell extracts using Ciphergen's ProteinChip® Technology (Ciphergen Biosystems Inc., Fremont, Calif.). Weak Cation Exchanger (WCX2) ProteinChip array (for profiling) and the pre-activated chip surface, PS1 (for affinity studies) were used for the identification of SP(1-4). The basic method, which was provided by Ciphergen was adjusted to optimize the analyses that follow. Stromal cells were washed with PBS and then subjected to repeated freeze-thaw. Cell-free lysates were prepared by centrifuging at 4° C. for 30 min/15,000 g. WCX2 was pre-treated with 10 mM HCl and 500 µL of each sample was spotted on the array using a bio-processor. The chips were incubated at room temperature for 30 min with vigorous shaking to ensure binding of sample to array. Subsequently, chips were washed with 5% Triton/PBS (2×) and with PBS (1×). A saturated solution of a-cyano-4-hydroxy cinnamic acid (CHCA) (Ciphergen Biosystems) was diluted at 1:50 in 50% acetonitrile and 0.5% trifluoroacetic acid. Diluted CHCA (0.5 µl) was added to the spots of the arrays and the chips were dried at room temperature. After this, chips were read on Ciphergen's Surface Enhanced Laser Desorption Ionization-Time of Flight Mass spectrometer (SELDI TOF-MS). Accurate mass was determined by collecting 150 averaged laser shots.

Stromal extracts from 48 h stimulated cultures were selected for further identification of immunoreactive SP(1-4). PS1 chips were pre-treated with 50% acetonitrile for 3 minutes and then incubated for 45 min with 10 µl of anti-SP at 1/500 dilution in PBS. Control spots contained non-immune rabbit serum. The arrays were blocked for 25 min with 1 M of ethanolamine and washed with PBS+0.5% Triton X (2×) and a final PBS wash step. 500 µl of cell extracts was incubated with the use of the bioprocessor. The chips were washed with PBS+Triton-x, PBS, rinsed with 5 mM Hepes and dried. CHCA was applied and SP(1-4) bound to the PS1 chip was analyzed as described above for the profiling studies.

B. Interactions between SCF and SP(1-4) on the Induction of TGF-β and TNF-α in BM Stroma The inhibitory effect of SP(1-4) on hematopoiesis is similar to NK-A, which is also a PPT-I peptide[5]. The suppressive effect of NK-A was partly mediated through the induction of TGF-β[5]. We therefore determined if SP(1-4) could induce two hematopoietic suppressors in BM stroma: TGF-β and TNF-α[28,30,31]. Table 1 shows that SP(1-4) significantly ($p<0.05$) increase the induction of both cytokines in BM stroma: Unstimulated, <5 pg TGF-β and <$10^{-4}$ pM TNF-α; Stimulated, 90±15 pg TGF-β and 40±4 pM TNF-α.

The next set of experiments determined whether SP(1-4) and SCF could affect the role of each other on the induction of TGF-β and TNF-α in BM stroma. Cells stimulated with SCF showed baseline TNF-α and TGF-β (Table 1). However, when SP(1-4) was added to the SCF-stimulated stroma, the levels of both cytokines were significantly ($p<0.05$) increased: TGF-β, <5 in the $1^{st}$ stimulation with SCF, which was changed to 80±8 pg/ml after a $2^{nd}$ stimulation with SP(1-4); TNF-α, 0.028±$10^{-4}$ in the $1^{st}$ stimulation to 31±2 pM in the $2^{nd}$ stimulation (Table 1).

To determine if SCF could affect the induction of TNF-α and TGF-β by SP(1-4), BM stroma was stimulated with SP(1-4) and 16 h later, cultures were subjected to a $2^{nd}$ stimulation with SCF. The results, shown in Table 1 indicated that TGF-β levels were reduced from 64±4 to <5 pg and TNF-α from 36±6 to 0.025±10⁻⁴ pM. The results indicate that SP(1-4) and SCF, negative and positive regulators of hematopoiesis respectively[8,20,32] showed different effects on the induction of TGF-β and TNF-α in BM stroma.

C. Effects of SP(1-4) on Early and Late Hematopoietic Progenitors

SP(1-4) inhibited the proliferation of hematopoietic progenitors (CFU-GM) in sera-containing cultures[8]. To verify that the sera did not contribute to this inhibitory effect of SP(1-4), clonogenic assays were repeated for CFU-GM (n=7) in sera-free cultures. The percent inhibition by SP(1-4) on CFU-GM in the sera-free cultures was significant (p<0.05): 55±4% for 1 nM SP(1-4) and 65±6% for 10 nM SP(1-4). This indicates that the inhibitory effect of SP(1-4) on CFU-GM was independent of the sera in the experimental assay. Since SP(1-4) induces the production of TGF-β and TNF-α (Table 1), which are inhibitors of hematopoiesis[30], studies were performed to determine if these cytokines could mediate the suppression of SP(1-4) on CFU-GM. Clonogenic assays were performed with 10 nM SP(1-4) and/or various concentrations of anti-TGF-β or anti-TNF-α. The data, shown in FIG. 1A, represent the point of maximal effect by the anti-TGF-β (0.5 μg/ml).

Anti-TGF-β showed significant (p<0.05) change in reversing the suppression of SP(1-4) on CFU-GM whereas anti-TNF-α showed no change (FIG. 1A). Equivalent concentration of non-immune rabbit and goat IgG showed no change in CFU-GM cultured with 10 nM SP(1-4) (data not shown). These results indicate that part of the suppressive effect of SP(1-4) on CFU-GM could be indirectly mediated by the production of TGF-β1 in BM stroma. TGF-β suppresses the proliferation of the more primitive hematopoietic progenitors[28].

To this end, we studied the effects of SP(1-4) on the proliferation of LTC-IC cells. The results are shown for CFU-GM cultured between weeks 10 and 12 (FIG. 1B). The pattern of inhibition by SP(1-4) on these relatively primitive hematopoietic progenitors was similar to CFU-GM. In the presence of anti-TGF-β1, there was partial, but significant (p<0.05) reversal in the inhibitory effect of SP(1-4) on the proliferation of the LTC-IC cells (FIG. 1B, 48±3 for media control and 37±4 for SP(1-4)+anti-TGF-β, ±SD). Anti-TNF-α showed no effect on the proliferation of LTC-IC cells (FIG. 1B). The results showed that SP(1-4) mediated the induction of TGF-β, which suppressed CFU-GM and partly inhibited the proliferation of LTC-IC cells. The secondary production of TNF-α by SP(1-4) in BM stroma showed no evidence as mediators in the hematopoietic effect of SP(1-4).

EXAMPLE III

A. Effects of SP(1-4) on NK-1 and NK-2 Expression

Since NK-1 and NK-2 receptors mediated the hematopoietic effects of the tachykinins[5], this section describes the studies and their results designed to further determine the interacting receptor for SP(1-4). Due to the lack of specific antibodies to the human NK-1 and NK-2 receptors, their detection by immunofluorescence was performed with the preferred ligand that was conjugated to biotin: SP for NK-1 and NK-A for NK-2[12]. Spantide, a pan-tachykinin antagonist that competes with the ligand for NK receptor binding was used to determine the specificity of binding. Representative results of five different labeling are shown in FIG. 2. Consistent with published reports[5], the results showed that SP binds to stromal cells in which NK-1 receptor was induced (SCF stimulation, FIG. 2B). NK-A did not bind to the SCF-stimulated stroma (FIG. 2C). These results are an internal control showing that the induction of NK-1 by cytokines correlates with reduced expression of NK-2[2,5]. Interestingly, stromal cells stimulated with SCF for 16 h and then a $2^{nd}$ stimulation with SP(1-4) showed a reduction in NK-1 expression (SP binding, FIG. 2E) and relatively brighter staining for NK-2 (NK-A binding, FIG. 2F). These results show that SP(1-4) reduced the expression of NK-1 in SCF-stimulated stroma with concomitant increase in the expression of NK-2.

Figure 3:
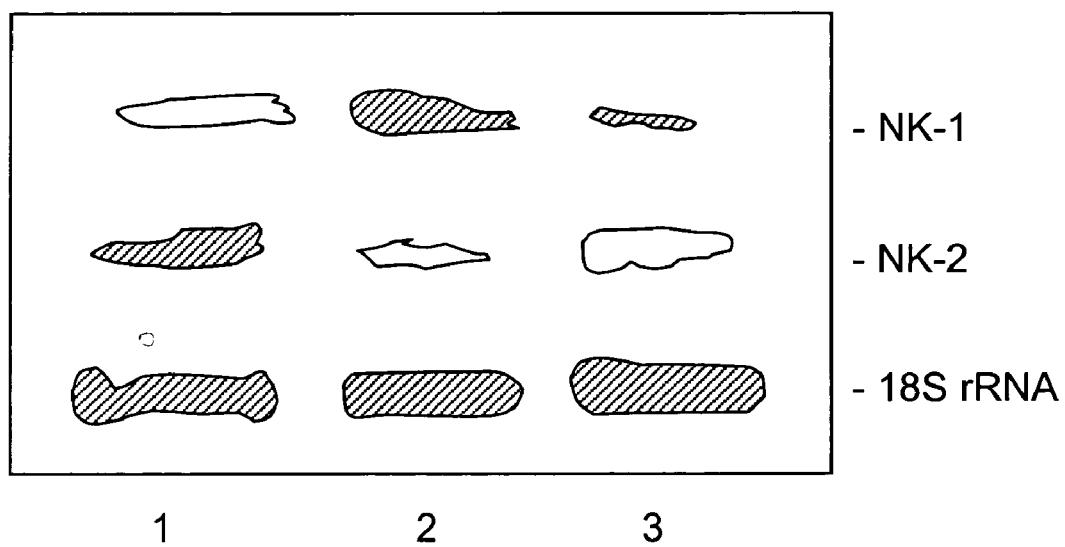
FIG. 3. NK-1 and NK-2 mRNA in BM stroma stimulated with 10 ng/ml SCF and/or 10 nM SP(1-4). Stroma was stimulated with SCF and at 16 h, cultures were terminated or washed and then restimulated with SP(1-4) for 16 h. Total RNA from each culture was studied for NK-1 and NK-2 mRNA by northern analyses. Lane 1: media alone; Lane 2: SCF; Lane 3: SCF-SP(1-4).

Quantitative RT-PCR was used to determine if the phenotypic expression of NK receptors (FIG. 2) correlated to the respective mRNA levels. The levels of NK-2 mRNA in unstimulated and SP(1-4) stimulated stroma were similar (Table 2). The level of NK-2 mRNA was however reduced following a $1^{st}$ stimulation with SCF (Table 2). This reduction in NK-2 mRNA was reversed following a $2^{nd}$ stimulation by SP(1-4) (Table 2). NK-1 mRNA levels were quantitated in BM stroma stimulated with SCF ($1^{st}$ stimulation). After 16 h, the time that NK-1 mRNA levels were increased (Table 2), stromal cells were re-stimulated with SP(1-4) ($2^{nd}$ stimulation). Compared to unstimulated stroma, the $2^{nd}$ stimulation showed a significant (p<0.05) increase in NK-1 mRNA levels (Table 2: 275±14 in SCF+SP(1-4) stimulation and <1 molecules/μg total RNA in unstimulated cells). The increase in NK-1 mRNA level by SCF+SP(1-4) was significantly reduced (p<0.05) compared to stroma stimulated with SCF alone (Table 2: 275±14 vs. 1480±34 molecules/μg total RNA). Northern blots with total RNA from selected experimental points supported the difference in NK-1 and NK-2 expression in unstimulated cultures (FIG. 3, Lane 1), SCF stimulation (FIG. 3, Lane 2) and cultures stimulated consecutively with SCF and SP(1-4) (FIG. 3, Lane 3). The results showed that SP(1-4) reduced the expression of NK-1, induced by SCF with concomitant increase in NK-2 expression.

B. Induction of NEP and correlation with detectable SP and SP(1-4)

Figure 4A:
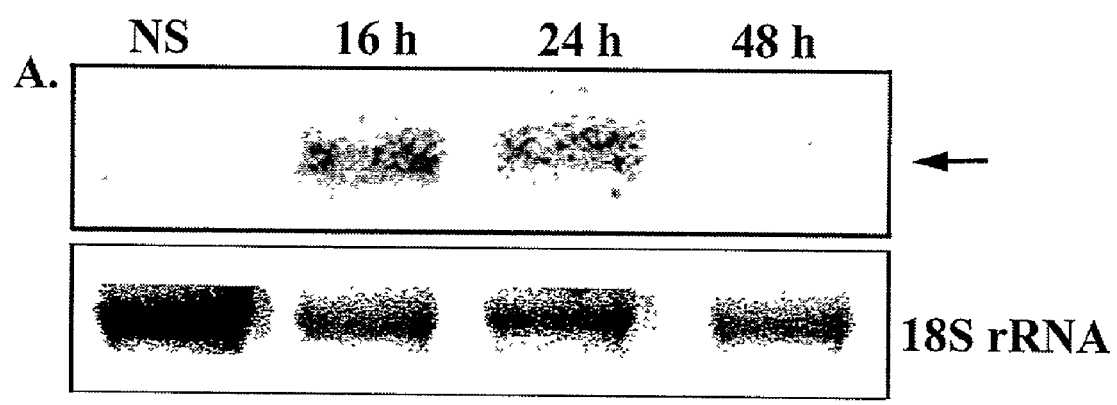
FIG. 4. Induction of NEP in BM stroma stimulated with SCF. Northern analyses determined steady state levels of mRNA for NEP at different times after stimulation of BM stroma with 10 ng/ml SCF (A). Arrow represents NEP mRNA and lower row represent 18S rRNA. NEP levels were normalized with 18 sRNA and represented as the fold change over unstimulated stroma (B). Representative blot from three different healthy donors.
Figure 4B:
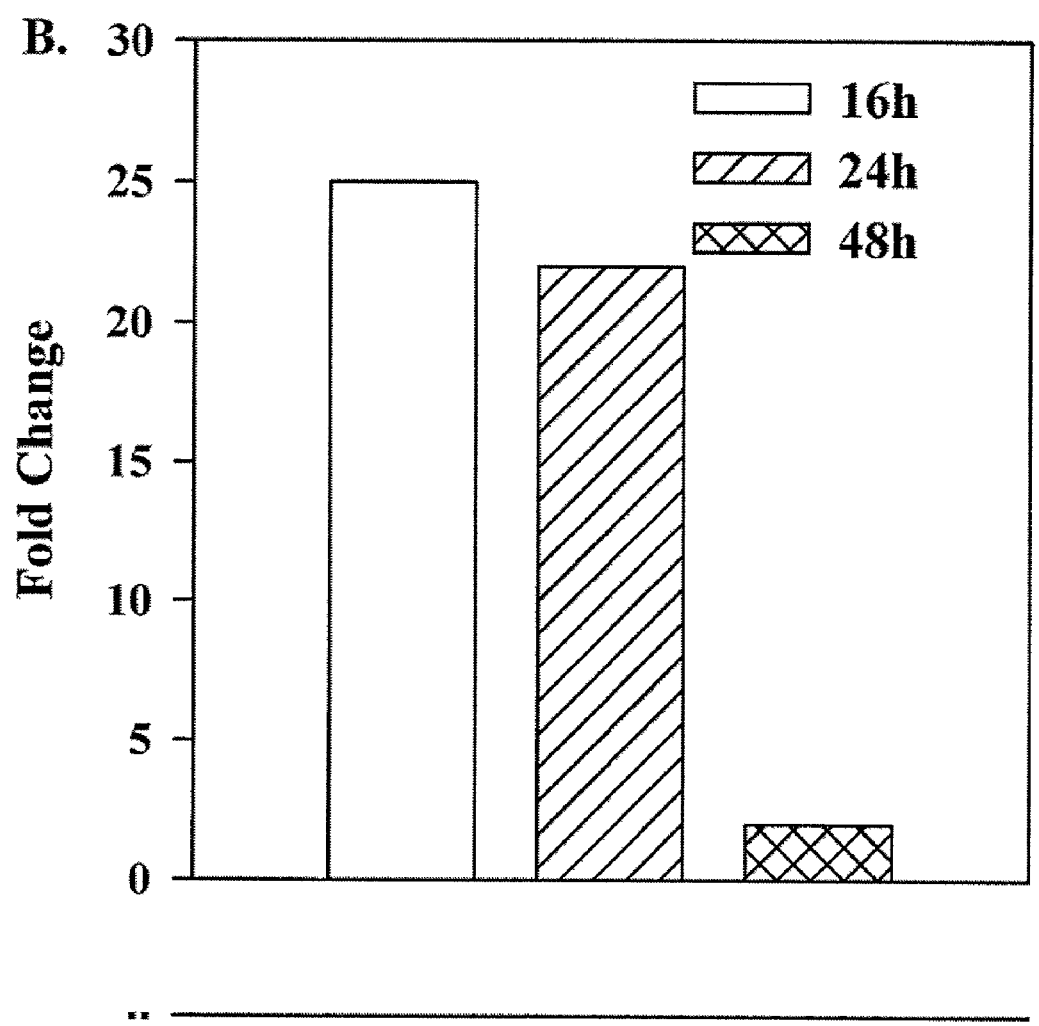

Total RNA from unstimulated and stimulated (10 ng/ml SCF) BM stroma was analyzed for steady state NEP mRNA levels by northern analyses. The results shown in FIG. 4A indicate single bands at the predicted size of 1.8 kb. Strong bands were observed at 16 h and 24 h with no detectable band at 48 h. FIG. 4B showed the fold change of normalized (18S rRNA) mRNA in stimulated over unstimulated stroma. The data indicate that the steady state mRNA for NEP is optimally increased by SCF after 16 h and remained detectable up to 24 h To determine if the induction of NEP correlated with the degradation of SP, timeline profiling studies were used to determine the change of SP to SP(1-4) in stromal cell extracts stimulated with 10 ng/ml of SCF. Analyses for SP and SP(1-4) were performed at different times using Ciphergen's ProteinChip Arrays. ELISA determined the levels of SP-IR in the supernatant and cell extracts of the stimulated stroma (5×10⁶ stroma). An affinity protein chip with mobilized anti-SP determined the presence of SP(1-4) in extracts from 48 h-stimulated stroma. The results showed <2 ng of SP-IR in unstimulated stroma (n=5). At 24 h, the total levels of SP-IR (supernatants and cell extracts) in stimulated stroma were 185±8 ng. SP levels were reduced to 12±5 ng at 48 h and to baseline levels (<2 ng) at 72 h (Table 3).

Since the small size of SP(1-4) poses limitation in its detection by methods similar to SP. ProteinChip arrays proved to be sensitive for the detection of SP(1-4). Stromal extracts were analyzed at 24, 48 and 72 h of SCF stimulation for peaks that are equivalent to SP and SP(1-4). A peak corresponding to the size of SP (FIG. 5A) was detected in five different samples, which disappeared at 48 and 72 h. During this same period (48 and 72 h), peaks corresponding to SP(1-4) were detected (FIG. 4B). To ascertain that the peak corresponding to 495 Da in the 48 h extract was indeed SP(1-4), the analyses was further studied with an affinity chip in which anti-SP was mobilized. Previous studies indicated that this antibody binds to SP(1-4), which explained a single peak at 495 Da (FIG. 5C) with no detection at ~1395 Da. Binding of non-immune rabbit sera to similar chips showed no detectable protein (data not shown). FIG. 5D summarizes the dynamics of SP and detectable SP(1-4) in SCF-stimulated stroma. The times that spanned reduced SP correlated with upregulation of NEP mRNA and the detection of molecules corresponding to 495 daltons, the size of SP(1-4).

C. 3-D Molecular Model of SP/SP(1-4)-NK-1 Interactions

Functional studies with specific NK-1 and NK-2 receptor antagonists indicated that the NK-1 subtype mediated the suppressive effects on hematopoiesis by SP(1-4)[8]. Studies described in this report however showed low levels of NK-1 mRNA in BM stroma stimulated with SP(1-4) compared to SCF (Table 2). Relatively reduced fluorescence was also observed for NK-1 labeling in stroma co-stimulated with SCF and SP(1-4) (FIG. 2). Due to the small size of SP(1-4), the use of standard binding assays pose technical problems to study its binding kinetics. We therefore used other approaches to understand SP(1-4)/NK-1 interactions. The first set of studies screened a random dodecapeptide library for SP(1-4) interacting sequences, which resulted in six clones that shared significant homology to NK-1 protein residues: Clones 7, 23 and 28 aligned with Exon 1 and clones 12, 19 and 26 with Exon 5 (FIG. 6). Alignment of the residues from the clones retrieved from the peptide library with NK-1 is shown at the bottom of FIG. 6.

Figure 7:
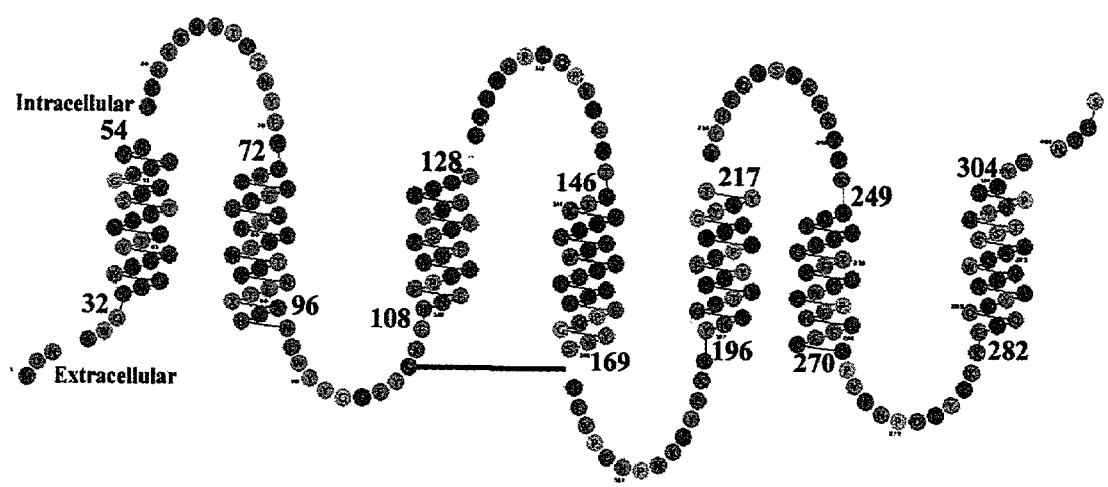
FIG. 7. Spatial assignment of NK-1 residues[27]. Segments of amino acid residues representing the TM regions of NK-1 and the related intra- and extra-cellular areas are shown in the 2D diagram.

To determine how the residues shown in FIG. 6 interact with SP(1-4), we used computer-assisted molecular modeling to generate a 3-D structure of SP and NK-1. This model was also needed to understand the paradigm of NK-1 mediating both positive and negative hematopoietic effects[2, 8]. We are unaware of a crystal or NMR structure for the extra- and intra-cellular loops of NK-1, which is a 7-TM, 407-residue, G-protein coupled receptor[10]. The spatial arrangement of its secondary structure is shown in FIG. 7 and the sequences shown for the TM regions was used to model the intra- and extra-cellular loops, using a loop search (SYBYL). The loop search algorithm searched a database of loops given a certain root mean square distance between two endpoints and the highest scoring homologue was selected between 24.3% and 46%.

A crystallized structure of SP was not available in any public database. There are interesting aspects of the sequence of SP, which has an amide group at the carboxyl terminal (FIG. 8A). The position of the two phenyl rings of the adjacent Phe[7,8] is optimal when they are trans to each other and their spatial arrangement lowers the probability for folding of the amino and carboxyl-tails toward each other. Pro[2] and Pro[4] create a kink in the head structure and the electrostatic interaction between positive and negative residues helps to stabilize the kink.

After generating the 3-D structures of SP and NK-1, they were docked by liphophilic, electrostatic, and H-bond interactions. The three types of interactions were performed to ensure that the docking was proper. Docking was done with and without the solvent-accessible surfaces, which were generated in SYBYL. MOLCAD was used to map the lipophilic, electrostatic and H-bond potentials on the surfaces. DOCK and Flexidock were used to prevent collision while docking the solvent accessible surfaces of SP and NK-1. The results, shown in FIGS. 8B and 8C are consistent with previous report[33], which indicated that the contact sites between SP and NK-1 are mainly on the extracellular loops and a few residues in the extracellular matrix-TM interface. The results are also consistent with the interacting sites retrieved from the peptide library, which indicated that Exons 1 and 5 of NK-1 are important for contact with SP(1-4) (FIGS. 6 and 8C). Exon 1 encodes TM 1-3, shown as α-helices 1-3 and Exon 7 encodes TM 7, shown as α-helix 7[34] (FIG. 8C). Indeed, the model, shown in FIGS. 8B and 8C indicate that the regions of SP(1-4) binds in the pocket within the domain formed by Exons 1 and 5. The results show that SP and SP(1-4) can bind into the same pocket within NK-1 and that they could compete for the same interacting site so that eventually SP cannot dock, which could lead to down regulation of NK-1.

EXAMPLE IV

As shown herein above, SP fragments exert immune and hematopoietic regulation[18,19]. The herein described methods show that SP(1-4) inhibits the proliferation of late and early hematopoietic progenitors. The 'parent' peptide, SP and cytokines associated with hematopoietic stimulation regulate the expression of each other leading to positive hematopoiesis[2]. The digestion of SP to SP(1-4) is a mechanism of hematopoietic feedback on the effects of SCF. This particular cytokine represents a model hematopoietic stimulator, which interact with SP to regulate the expression of each other[20,21]. Induction of the following was studied: negative hematopoietic regulators, TGF-β and TNF-α, the receptors for SP and its fragments (NK-1 and NK-2) and induction of NEP mRNA. SP/SP(1-4)-NK-1 interactions were examined in timeline proteomic studies: screening of a random dodecapeptide library, ProteinChip Array and by 3-D molecular modeling.

Figure 9:
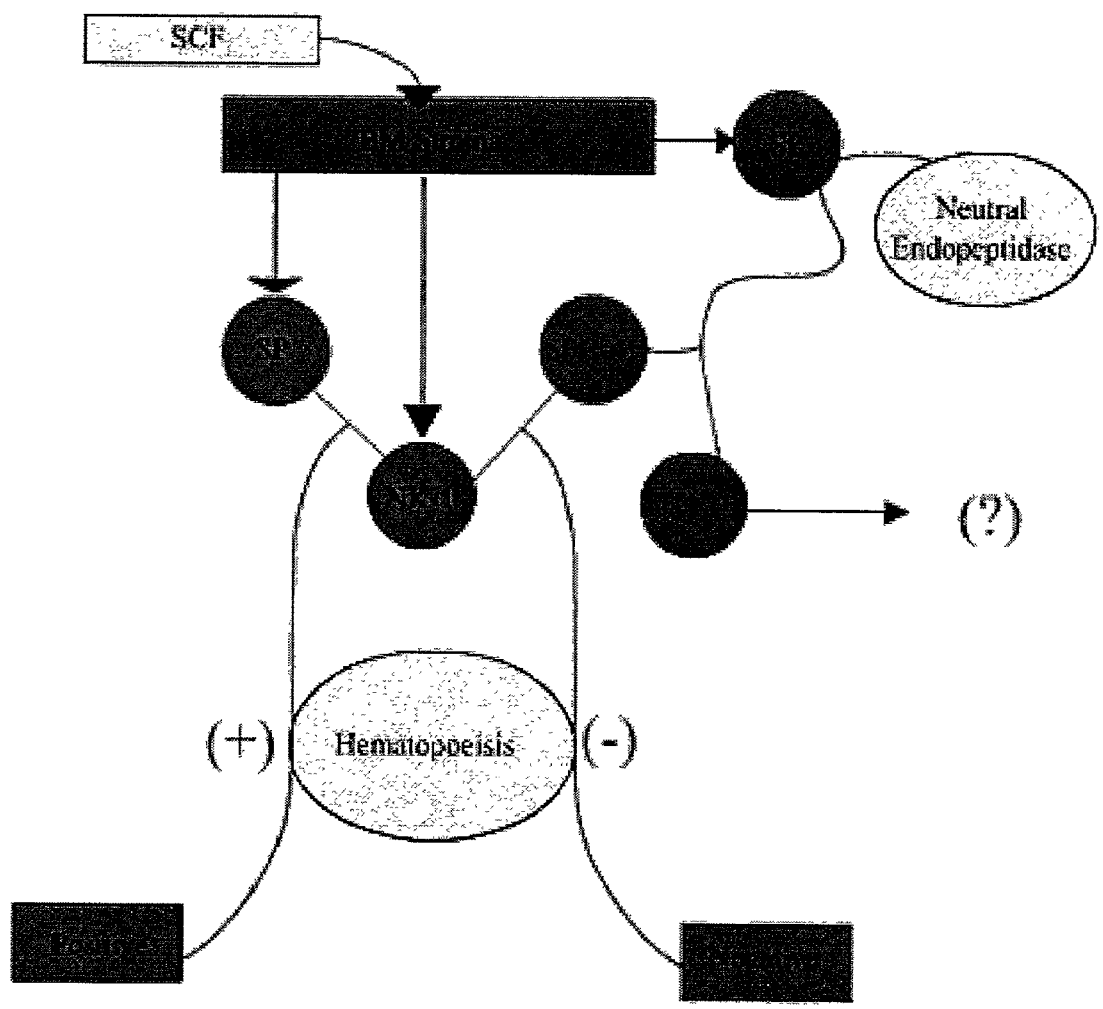
FIG. 9. Model of hematopoietic feedback by SP(1-4). SCF mediated the release of SP from BM stroma with concomitant expression of NK-1. SP-NK-1 interaction leads to hematopoietic stimulation (+). NEP, which is also induced in the SCF-stimulated stroma uses SP as its substrate to produce SP(1-4). Interaction between SP(1-4) and NK-1 negatively regulate the stimulatory effect of SP on hematopoiesis (−).

A cartoon representing the findings of this study is shown in FIG. 9. We show a mechanism in which the PPT-I gene could be involved in modulating hematopoiesis. In the BM, SP(1-4) could be derived through enzymatic digestion by endogenous endopeptidases[6,7]. Since SP(4-11) exerts stimulatory effects similar to the parent peptide[8], the effects of the amino terminal fragment raised the question of SP(1-4) being effective as a hematopoietic feedback inhibitor, while the carboxyl fragment might be in the vicinity of the receptor. The experimental evidence suggests that SP(5-11) might be quickly degraded to a non-functional form by other endopeptidases that can use the longer carboxyl fragment as a substrate[15,16]. Ongoing studies using Ciphergen's ProteinChip technique showed no evidence of SP(5-11). The reason for this might be due to rapid degradation of the carboxyl fragment by other endopeptidases, which would result in SP(1-4) alone.

Furthermore, the negative hematopoietic effects of SP(1-4) is mediated through NK-1[8]. This is a paradox since the NK-1 receptor mediates positive hematopoietic responses by interacting with SP[2]. Although a negative hematopoietic response was expected to be mediated through NK-2 receptor[5], screening of the peptide library did not show potential interacting site for SP(1-4) within NK-2 (FIG. 6). The lack of evidence for NK-2 as a mediator in the effect of SP(1-4) was puzzling since SP(1-4) did not induce the other NK subtype (NK-1) in stromal cells (Table 2). An understanding of the role of NK-1 in SP(1-4) effect was provided by the appearance of SP(1-4) in SCF-stimulated cells (FIG. 5) while NK-1 expression was still upregulated (FIG. 2, Table 2). Analyses of these results suggest that the induction of NK-1 by SCF was blunted after the change of SP to SP(1-4) and with time, membrane expression of NK-1 was reduced (FIG. 2). The significance of this reduction is the provision of a feedback mechanism on the effects of SCF.

FIG. 5C summarizes the dynamics between SP and SP(1-4). SP is first detected in stromal cells stimulated with SCF. This is followed by the appearance of NEP and then the degradation of SP to SP(1-4). This model does not explain the signaling pathway mediated by SP(1-4) to induce TGF-β and TNF-α (Table 1) however, from the results detailed herein such an induction can be seen. There were significant differences in the levels of TGF-β and TNF-α in stroma stimulated with SP(1-4) during the $1^{st}$ and $2^{nd}$ stimulation (Table 1). Since the cytokine quantitations for each set of stimulation was performed separately, the differences suggest that the optimal times for the induction of TNF-α and TGF-β were 16 h, which was followed by reduced gene expression. The increased levels of TGF-β and TNF-α in stroma stimulated with SP(1-4) can not be due to the initial stimulation with SCF since the levels were similar to stroma stimulated with only SP(1-4) (Table 1).

The 3-D structure of NK-1 and SP allows assumptions regarding interactions between NK-1 and SP and provides a possible explanation for the function of SP(1-4) in hematopoietic feedback. Both SP and its fragment SP(1-4) could occupy the same pocket within NK-1 (FIGS. 8B and 8C). A common pocket for both SP and SP(1-4) indicated that in the presence of SP(1-4), the 'fit' for SP within NK-1 would be hindered. In the absence of SP-NK-1 interactions, the production of stimulatory hematopoietic regulators such as cytokines could be down regulated[2]. Since these cytokines induce the expression of NK-1, then the loss of SP-NK-1 could result in down regulation NK-1 and switch to alternate functions by SP(1-4)-NK-1 (FIG. 8C). A possibility for this is shown by the production of TGF-β and TNF-α by SP(1-4) in BM stroma (Table 1).

The induction of TGF-β and TNF-α, hematopoietic inhibitors[28,30] could be blunted by SCF (Table 1), which would promote a switch from negative to positive hematopoiesis. Also, NK-A, a PPT-I gene-derived peptide that exerts hematopoietic suppression[5] could be a substrate of endogenous endopeptidases[36]. Degradation of NK-A could make the BM more amenable to hematopoietic stimulation. Another example is SP being able to protect itself from degradation. This protection could occur by SP being able to down regulate the expression of particular endopeptidases, such as CD13 and its complexing to a fibronectin, which is a relatively large molecule[29,37]. CD13 is the second enzyme following neutral endopeptidase that could degrade the carboxyl fragment of SP[38]. Reduced expression of CD13 would leave SP intact for hematopoietic stimulation.

By using the conventions head (residues 1-4) and tail (residues 5-11) for SP, certain assumptions can be made about the structure of SP. The model, shown in FIG. 8A, indicates no helical structure of SP but a curve in the head region. However, Cowsik et al.[40] reported a structure of SP that is partly helical in the tail region when bound to lipids. Although we used a different 3-D structure of SP, the structure of Cowsik et al.[40] could also dock to the NK-1 model, shown in FIGS. 8B and 8C. Using molecular dynamics, the model shown in this study is the lowest in energy (−58.5 kcals) although it is possible that the bioactive peptide could be in a higher energy confirmation.

SP binds to NK-1 within an interface between the cell membrane and the extracellular matrix[33,41]. The confirmation of SP-NK-1, shown in the 3-D model (FIGS. 8B and 8C) allows easy access for endopeptidases to cleave SP. The model accounts for a structural difference between SP(1-4) and SP(5-11) and also for electrostatic (FIG. 8B) and lipophilic (not shown) complementarities between SP and NK-1. We hypothesize that the message sequence of SP, located within the carboxyl terminal[42] cannot activate NK-1 if the address sequence, which includes SP(1-4) occupies the pocket (FIG. 8C). Without proper configuration of the message, the peptide would not be able to activate the G-protein through classical mechanism. However SP(1-4), an address alone mediates signaling through the NK-1 receptor. This is demonstrated by the biological functions mediated by SP(1-4) (Table 1, FIG. 1).

The biology of PPT-I peptides and their fragment is not only applicable to the BM but also to other lymphoid organs[2] and would unravel the 'fine-tuned' interplay between NK-A, endopeptidases, SP and other hematopoietic/inflammatory factors. The inhibitory hematopoietic effects of SP(1-4) suggest that this peptide can influence the self-renewal capabilities of the hematopoietic stem cells.

As stated above, the foregoing is intended to be illustrative of the embodiments of the present invention, and are not intended to limit the invention in any way. Although the invention has been described with respect to the specific modifications described above, the details thereof are not to be construed as limitations, for it will be apparent that various equivalents, changes and modifications may be resorted to without departing from the spirit and scope thereof and it is understood that such equivalent embodiments are to be included herein.

TABLE 1

Induction of TGF-β and TNF-α in BM stroma stimulated with SP(1-4).

| | TGF-β (pg/ml) | | TNF-α (pM) | |
| --- | --- | --- | --- | --- |
| | $1^{st}$ stimulation | $2^{nd}$ stimulation | $1^{st}$ stimulation | $2^{nd}$ stimulation |
| Unstimulated | <5 | <5 | $0.01 \pm 10^{-4}$ | $0.015 \pm 10^{-4}$ |
| SCF | <5 | | $0.023 \pm 10^{-4}$ | |
| →SP(1-4) | | *80 ± 8 | | *31 ± 2 |
| →SCF | | <5 | | $0.028 \pm 10^{-4}$ |
| SP(1-4) | *90 ± 15 | | *40 ± 4 | |
| →SP(1-4) | | *64 ± 4 | | *36 ± 6 |
| →SCF | | <5 | | $0.025 \pm 10^{-4}$ |

Stimuli shown in column 1: $1^{st}$, left of arrow; $2^{nd}$, right of arrow.

BM stroma was stimulated with 10 nM SP(1-4) or 10 ng/ml SCF ($1^{st}$ stimulation). After 16 h, cells were harvested or cultures were re-stimulated for 16 h ($2^{nd}$ stimulation) with 10 nM SP(1-4) or 10 ng/ml SCF. TGF-β and TNF-α levels were determined in the total volume of supernatants and cell extracts, obtained from one flask of stromal cells. The results are represented as the mean±SD of the total concentration (secreted and cell-bound/106 stromal cells). p<0.05 vs. unstimulated or SCF.

TABLE 2

Regulation of NK-1 and NK-2 by SP(1-4) in BM stroma.

| | 1st stimulation | | | 2nd stimulation | | |
|---|---|---|---|---|---|---|
| Unstimulated | <1 | 464 ± 20 | 5 | <1 | 01 ± 18 | 3 |
| SCF | *1550 ± 26 | 17 ± 3 | 640 ± 15 | | | |
| →SP(1-4) | | | | 275 ± 14 | **550 ± 20 | |
| →SCF | | | | *1480 ± 34 | 10 ± 2 | 45 ± 4 |
| SP(1-4) | <1 | **510 ± 15 | <1 | | | |
| →SP(1-4) | | | | <1 | **484 ± 10 | <1 |
| →SCF | | | | *1026 ± 24 | 26 ± 12 | 650 ± 10 |

Stimuli shown in column 1: 1st, left of arrow; 2nd, right of arrow.

BM stroma was stimulated with 10 nM SP(1-4) or 10 ng/ml SCF for 16 h (1st stimulation). After this, cultures were washed and then re-stimulated further for 16 h with similar concentrations of SP(1-4) or SCF (2nd stimulation). NK-1, NK-2 and β-PPT-I mRNA levels were quantitative by RT-PCR. The results are represented as the mean±SD, n=6. Each experiment was performed with a different BM donor. $p<0.05$: * vs. unstimulated or SP(1-4). $p>0.05$: ** vs. unstimulated or SP(1-4).

REFERENCES

1. Janowska-Wieczorek A, Majka M, Ratajczak J, Ratajczak M Z. Autocrine/paracrine mechanisms in human hematopoiesis. Stem Cells. 2001;19:99–107.
2. Rameshwar P. Substance P: A regulatory neuropeptide for hematopoiesis and immune functions. Clin Immunol Immunopath. 1997;85, 129–133.
3. Maloof P B, Joshi D D, Qian J, Gascón P, Singh D, Rameshwar P. Induction of Preprotachykinin-I and Neurokinin-1 by adrenocorticotropin and prolactin. Implication for neuroendocrine-immune-hematopoietic axis J Neuroimmunol. 2000;112:188–196.
4. Weissman I L. Translating stem and progenitor cell biology to the clinic: barriers and opportunities. Science. 2000;287:1442–1446.
5. Rameshwar P, Poddar A, Gascón P. Hematopoietic regulation mediated by interactions among the neurokinins and cytokines Leuk Lymphoma. 1997;28:1–10.
6. Mentlein R. Dipeptidyl-peptidase IV (CD26)-role in the inactivation of regulatory peptides. Reg Peptides. 1999; 85:9–24.
7. Van der Velden V H J, Hulsmann A R. Peptidases: structure, function and modulation of peptide-mediated effects in the human lung. Clin Exp Allergy. 1999;29: 445–456.
8. Qian J, Haider A, Teli T, Tuan T, Gascón P, Rameshwar P. In: Talwar G P, Nath I, Ganguly N K, Rao K V S, eds. Effects of SP(1-4) on cobblestone-forming cells. Implications for endopeptidases as hematopoietic regulators. Proceedings of the tenth International Congress of Immunology. Monduzzo, Bologna, Italy. 1998:575–581.
9. Maggi C A. Tachykinins in the autonomic nervous system. Pharmacol Res. 1996;33: 161–170.
10. Maggi C A, Schwartz T W. The dual nature of the tachykinin NK1 receptor. TiPS. 197;18:351–355.
11. Quartara L, Maggi C A. The tachykinin NK1 receptor. Part I: ligands and mechanisms of cellular activation. Neuropeptides. 1997;31:537–563.
12. Regoli D, Nguyen Q T, Jukic D. Neurokinin receptor subtypes characterized by biological assays. Life Sci. 1994;54:2035–2047.
13. van der Velden, V H J, Naber B A E, van der Spoel P, Hoogsteden H C, Versnel M A. Cytokines and glucocorticoids modulate human bronchial epithelial cell peptidases. Cytokine. 1998;10:55–65.
14. Solan N J, Ward P E, Sanders S P, Towns M C, Bathon J M. Soluble recombinant neutral endopeptidase (CD10) as a potential anti-inflammatory agent. Inflammation. 1998;22:107–121.
15. Ahmad S, Wang L, Ward P E. Dipeptidyl (amino) peptidase IV and aminopeptidase M metabolize circulating substance P in vivo. Pharmacol Exp Therapeut. 1992; 260:1257–1261.
16. Vanhoof G, Goossens F, De Meester I, Hendricks D, Scharpe S. Proline motifs in peptides and their biological processing. FASEB J. 1995;9:736–744.
17. Stefano G B, Kushnerik V, Rodriguez M, Bilfinger T V. Inhibitory effect of morphine on granulocyte stimulation by tumor necrosis factor and substance P. Int J Immunopharmacol. 1994;16:329–334.
18. Rameshwar P, Gascón P, Ganea D. Stimulation of interleukin 2 production in murine lymphocytes by substance P and related tachykinins J Immunol. 1993;151: 2484–2496.
19. Rameshwar P, Ganea D, Gascón P. Induction of IL-3 and GM-CSF by substance P in bone marrow cells is partially mediated through the release of IL-1 and IL-6. J Immunol. 1994;152:4044–4054.
20. Bodine D M, Seidel N E, Zsebo K M, Orlic D. In vivo administration of stem cell factor to mice increases the absolute number of pluripotent hematopoietic stem cells. Blood. 1993;82:445–455.
21. Qian J, Yehia G, Molina C et al., Cloning of human preprotachykinin-I promoter and the role of adenosine 5-monophosphate response elements in its expression by IL-1 and stem cell factor. J Immunol. 2001;166:2553–2561.
22. Rameshwar P, Gascón P. Induction of negative hematopoietic regulators by neurokinin-A in bone marrow stroma Blood. 1996;88:98–106.
23. Rameshwar P, Denny T, Stein D, Gascón P. Adhesion of monocytes from patients with bone marrow fibrosis is required for the production of fibrogenic cytokines. Potential role for IL-1 and TGF-β. J Immunol. 1994;153: 2819–2830.
24. Singh D, Joshi D D, Harneed M, Qian J, Gascón P, Maloof P B, Mosenthal A, Rameshwar P. Increased expression of preprotachykinin-I and neurokinin receptors in human breast cancer cells. Implications for bone marrow metastasis Proc Nat'l Acad Sci USA. 2000;97: 388–393.
25. Rameshwar P, Narayanan R, Qian J, Denny T N, Colon C, Gascón P. NF-κB as a central mediator in the induction 26. Gerard N P, Garraway L A, Eddy R L, Shows Jr T B, Iijima H, Paquet J L, Gerard C. Human substance P receptor K-1): organization of the gene, chromosome localization, and functional expression of cDNA clones. Biochemistry. 1991;30:10640–10646.
27. Baldwin J M, Schertler G F, Unger V M. An alpha-carbon template for the transmembrane helices in the rhodopsin family of G-protein-coupled receptors. J Mol Biol. 1997;272:144–164.
28. Fortunel N O, Hatzfeld A, Hatzfeld J A. Transforming growth factor-β: pleiotropic role in the regulation of hematopoiesis. Blood. 2000;96:2022–2036.
29. Rameshwar P, Joshi D D, Yadav P et al., Mimicry between neurokinin-1 and fibronectin may explain the transport and stability of increased substance P-immunoreactivity in patients with bone marrow fibrosis. Blood. 2001;97:3025–3031.
30. Mayani H, Little M T, Dragowska W, Thornbury G, Lansdorp P M. Differential effects of the hematopoietic inhibitors MIP-1α, TGF-β, and TNF-α on cytokine-induced proliferation of subpopulations of CD34+ cells purified from cord blood and fetal liver. Exp Hematol. 1995;23:422–427.
31. Muller-Sieburg C E, Deryugina E. The stromal cells' guide to the stem cell universe. Stem Cells. 1995;13:477–486.
32. Rameshwar P, Gascón P. Substance P (SP) mediates production of stem cell factor and interleukin-1 in bone marrow stroma: Potential autoregulatory role for these cytokines in SP receptor expression and induction Blood. 1995;86:482–490.
33. Turcatti G, Zoffmann S, Lowe III J A, Drozda S E, Chassaing G, Schwartz T W, Chollet A. Characterization of non-peptide antagonist and peptide agonist binding sites of the NK1 receptor with fluorescent ligands. J Biol Chem. 1997;272:21167–21175.
34. Huang R R C, Yu H, Strader C, Fong T M. Localization of the ligand binding site of the NK-1 receptor: Interpretation of chimeric mutations and single-residue substitutions. Mol Pharmacol. 1994;45:690–695.
35. McDonald P H, Chow C W, Miller W E et al., Beta-arrestin 2: a receptor-regulated MAPK scaffold for the activation of JNK3. Science. 2000;290:1574–1577.
36. Crimi N, Palermo F, Oliveri R, Polosa R, Magri S, Mistretta A. Inhibition of neural endopeptidase potentiates bronchoconstriction induced by neurokinin A in asthmatic patients. Clin Exp Allergy. 1994;24:115–120.
37. Look A T, Ashmun R A, Shapiro L H, Peiper S C. Human myeloid plasma membrane glycoprotein CD13 (gp 150) is identical to aminopeptidase N. J Clin Invest. 1989;83:1299–1307.
38. Xu Y, Wellner D, Scheinberg D A. Substance P and bradykinin are natural inhibitors of CD13/aminopeptidase N. Biochem Biophy Res Comm. 1995;208:664–674.
39. Covas M J, Pinto L A, Victorino R M M. Effects of substance P on human T cell function and the modulatory role of peptidase inhibitors. Int J Clin Lab Res. 1997;27:129–134.
40. Cowsil S M, Lucke C, Ruterjans H. Lipid-induced conformation of substance P. J Biomol Struc & Dynamics. 1997;15:27–33.
41. Amati V, Werge T M, Cattaneo A, Tramontano A. Identifying a putative common binding site shared by SP receptor and an anti-substance P monoclonal antibody. Protein Engineering. 1995;8:403–408.
42. Yokota Y, Akazawa C, Ohkubo H, Nakanishi S. Delineation of structural domains involved in the subtype specificity of tachykinin receptors through chimeric formation of substance P/substance K receptors. EMBO J. 1992;11:3585–3591.
43. Li Xiao-Mei, Ezan E, Bindoula G et al., Chronopharmacologic aspects of continuous AcSDKP infusion in mice. Exp Hematol 1999;27:19–27.
44. Paukovits W R, Paukovits J B, Moser M-H, Konstantinov S, Schulte-Hermann R. Activated granulocytes oxidize the endogenous stem cell inhibitory peptide pGlu-Glu-Asp-Cys-Lys (pEEDCK) to the stimulatory dimmer: a redox-mediated mechanism for deman-induced hematopoietic regulation. Exp Hematol 1998;26:851–858.

What is claimed is:

1. A method of protecting stem cells in a subject about to undergo or undergoing cancer therapy, comprising administering to a subject a pharmaceutical composition comprising a biologically effective amount of Substance P polypeptide SEQ ID NO:2 and an acceptable carrier.

2. The method of claim 1, wherein the stem cell is selected from the group consisting of lymphoid, myeloid, LTC-IC, CFU-GM, CFU-B, burst-forming unit-erythroid cell, colony forming unit-erythroid and colony forming unit-megakaryocyte.

* * * * *

SEQUENCE LISTING

```
<160> NUMBER OF SEQ ID NOS: 4

<210> SEQ ID NO 1
<211> LENGTH: 12
<212> TYPE: DNA
<213> ORGANISM: Homo sapiens
<220> FEATURE:
<221> NAME/KEY: CDS
<222> LOCATION: (1)..(12)
<223> OTHER INFORMATION:

<400> SEQUENCE: 1 aga cca aaa cca                                                       12
Arg Pro Lys Pro
1

<210> SEQ ID NO 2
<211> LENGTH: 4
<212> TYPE: PRT
<213> ORGANISM: Homo sapiens

<400> SEQUENCE: 2
```

Arg Pro Lys Pro
1

<210> SEQ ID NO 3
<211> LENGTH: 5508
<212> TYPE: DNA
<213> ORGANISM: Homo sapiens
<220> FEATURE:
<221> NAME/KEY: CDS
<222> LOCATION: (12)..(2264)
<223> OTHER INFORMATION:

<400> SEQUENCE: 3

```
gattttaggt g atg ggc aag tca gaa agt cag atg gat ata act gat atc         50
          Met Gly Lys Ser Glu Ser Gln Met Asp Ile Thr Asp Ile
            1               5                  10 aac act cca aag cca aag aag aaa cag cga tgg act cga ctg gag atc         98
Asn Thr Pro Lys Pro Lys Lys Lys Gln Arg Trp Thr Arg Leu Glu Ile
 15                  20                  25 agc ctc tcg gtc ctt gtc ctg ctc acc atc ata gct gtg aga atg            146
Ser Leu Ser Val Leu Val Leu Leu Thr Ile Ile Ala Val Arg Met
 30                  35                  40                  45 atc gca ctc tat gca acc tac gat gat ggt att tgc aag tca tca gac        194
Ile Ala Leu Tyr Ala Thr Tyr Asp Asp Gly Ile Cys Lys Ser Ser Asp
                 50                  55                  60 tgc ata aaa tca gct gct cga ctg atc caa aac atg gat gcc acc act        242
Cys Ile Lys Ser Ala Ala Arg Leu Ile Gln Asn Met Asp Ala Thr Thr
         65                  70                  75 gag cct tgt aga gac ttt ttc aaa tat gct tgc gga ggc tgg ttg aaa        290
Glu Pro Cys Arg Asp Phe Phe Lys Tyr Ala Cys Gly Gly Trp Leu Lys
     80                  85                  90 cgt aat gtc att ccc gag acc agc tcc cgt tac ggc aac ttt gac att        338
Arg Asn Val Ile Pro Glu Thr Ser Ser Arg Tyr Gly Asn Phe Asp Ile
 95                 100                 105 tta aga gat gaa cta gaa gtc gtt ttg aaa gat gtc ctt caa gaa ccc        386
Leu Arg Asp Glu Leu Glu Val Val Leu Lys Asp Val Leu Gln Glu Pro
110                 115                 120                 125 aaa act gaa gat ata gta gca gtg cag aaa gca aaa gca ttg tac agg        434
Lys Thr Glu Asp Ile Val Ala Val Gln Lys Ala Lys Ala Leu Tyr Arg
                130                 135                 140 tct tgt ata aat gaa tct gct att gat agc aga ggt gga gaa cct cta        482
Ser Cys Ile Asn Glu Ser Ala Ile Asp Ser Arg Gly Gly Glu Pro Leu
        145                 150                 155 ctc aaa ctg tta cca gac ata tat ggg tgg cca gta gca aca gaa aac        530
Leu Lys Leu Leu Pro Asp Ile Tyr Gly Trp Pro Val Ala Thr Glu Asn
    160                 165                 170 tgg gag caa aaa tat ggt gct tct tgg aca gct gaa aaa gct att gca        578
Trp Glu Gln Lys Tyr Gly Ala Ser Trp Thr Ala Glu Lys Ala Ile Ala
175                 180                 185 caa ctg aat tct aaa tat ggg aaa aaa gtc ctt att aat ttg ttt gtt        626
Gln Leu Asn Ser Lys Tyr Gly Lys Lys Val Leu Ile Asn Leu Phe Val
190                 195                 200                 205 ggc act gat gat aag aat tct gtg aat cat gta att cat att gac caa        674
Gly Thr Asp Asp Lys Asn Ser Val Asn His Val Ile His Ile Asp Gln
                210                 215                 220 cct cga ctt ggc ctc cct tct aga gat tac tat gaa tgc act gga atc        722
Pro Arg Leu Gly Leu Pro Ser Arg Asp Tyr Tyr Glu Cys Thr Gly Ile
        225                 230                 235 tat aaa gag gct tgt aca gca tat gtg gat ttt atg att tct gtg gcc        770
Tyr Lys Glu Ala Cys Thr Ala Tyr Val Asp Phe Met Ile Ser Val Ala
    240                 245                 250
```

-continued

```
aga ttg att cgt cag gaa gaa aga ttg ccc atc gat gaa aac cag ctt      818
Arg Leu Ile Arg Gln Glu Glu Arg Leu Pro Ile Asp Glu Asn Gln Leu
    255                 260                 265 gct ttg gaa atg aat aaa gtt atg gaa ttg gaa aaa gaa att gcc aat      866
Ala Leu Glu Met Asn Lys Val Met Glu Leu Glu Lys Glu Ile Ala Asn
270                 275                 280                 285 gct acg gct aaa cct gaa gat cga aat gat cca atg ctt ctg tat aac      914
Ala Thr Ala Lys Pro Glu Asp Arg Asn Asp Pro Met Leu Leu Tyr Asn
                290                 295                 300 aag atg aga ttg gcc cag atc caa aat aac ttt tca cta gag atc aat      962
Lys Met Arg Leu Ala Gln Ile Gln Asn Asn Phe Ser Leu Glu Ile Asn
            305                 310                 315 ggg aag cca ttc agc tgg ttg aat ttc aca aat gaa atc atg tca act     1010
Gly Lys Pro Phe Ser Trp Leu Asn Phe Thr Asn Glu Ile Met Ser Thr
        320                 325                 330 gtg aat att agt att aca aat gag gaa gat gtg gtt gtt tat gct cca     1058
Val Asn Ile Ser Ile Thr Asn Glu Glu Asp Val Val Val Tyr Ala Pro
    335                 340                 345 gaa tat tta acc aaa ctt aag ccc att ctt acc aaa tat tct gcc aga     1106
Glu Tyr Leu Thr Lys Leu Lys Pro Ile Leu Thr Lys Tyr Ser Ala Arg
350                 355                 360                 365 gat ctt caa aat tta atg tcc tgg aga ttc ata atg gat ctt gta agc     1154
Asp Leu Gln Asn Leu Met Ser Trp Arg Phe Ile Met Asp Leu Val Ser
                370                 375                 380 agc ctc agc cga acc tac aag gag tcc aga aat gct ttc cgc aag gcc     1202
Ser Leu Ser Arg Thr Tyr Lys Glu Ser Arg Asn Ala Phe Arg Lys Ala
            385                 390                 395 ctt tat ggt aca acc tca gaa aca gca act tgg aga cgt tgt gca aac     1250
Leu Tyr Gly Thr Thr Ser Glu Thr Ala Thr Trp Arg Arg Cys Ala Asn
        400                 405                 410 tat gtc aat ggg aat atg gaa aat gct gtg ggg agg ctt tat gtg gaa     1298
Tyr Val Asn Gly Asn Met Glu Asn Ala Val Gly Arg Leu Tyr Val Glu
    415                 420                 425 gca gca ttt gct gga gag agt aaa cat gtg gtc gag gat ttg att gca     1346
Ala Ala Phe Ala Gly Glu Ser Lys His Val Val Glu Asp Leu Ile Ala
430                 435                 440                 445 cag atc cga gaa gtt ttt att cag act tta gat gac ctc act tgg atg     1394
Gln Ile Arg Glu Val Phe Ile Gln Thr Leu Asp Asp Leu Thr Trp Met
                450                 455                 460 gat gcc gag aca aaa aag aga gct gaa gaa aag gcc tta gca att aaa     1442
Asp Ala Glu Thr Lys Lys Arg Ala Glu Glu Lys Ala Leu Ala Ile Lys
            465                 470                 475 gaa agg atc ggc tat cct gat gac att gtt tca aat gat aac aaa ctg     1490
Glu Arg Ile Gly Tyr Pro Asp Asp Ile Val Ser Asn Asp Asn Lys Leu
        480                 485                 490 aat aat gag tac ctc gag ttg aac tac aaa gaa gat gaa tac ttc gag     1538
Asn Asn Glu Tyr Leu Glu Leu Asn Tyr Lys Glu Asp Glu Tyr Phe Glu
    495                 500                 505 aac ata att caa aat ttg aaa ttc agc caa agt aaa caa ctg aag aag     1586
Asn Ile Ile Gln Asn Leu Lys Phe Ser Gln Ser Lys Gln Leu Lys Lys
510                 515                 520                 525 ctc cga gaa aag gtg gac aaa gat gag tgg ata agt gga gca gct gta     1634
Leu Arg Glu Lys Val Asp Lys Asp Glu Trp Ile Ser Gly Ala Ala Val
                530                 535                 540 gtc aat gca ttt tac tct tca gga aga aat cag ata gtc ttc cca gcc     1682
Val Asn Ala Phe Tyr Ser Ser Gly Arg Asn Gln Ile Val Phe Pro Ala
            545                 550                 555 ggc att ctg cag ccc ccc ttc ttt agt gcc cag cag tcc aac tca ttg     1730
Gly Ile Leu Gln Pro Pro Phe Phe Ser Ala Gln Gln Ser Asn Ser Leu
```

-continued

```
            560             565             570
aac tat ggg ggc atc ggc atg gtc ata gga cac gaa atc acc cat ggc    1778
Asn Tyr Gly Gly Ile Gly Met Val Ile Gly His Glu Ile Thr His Gly
        575             580             585 ttc gat gac aat ggc aga aac ttt aac aaa gat gga gac ctc gtt gac    1826
Phe Asp Asp Asn Gly Arg Asn Phe Asn Lys Asp Gly Asp Leu Val Asp
590             595             600             605 tgg tgg act caa cag tct gca agt aac ttt aag gag caa tcc cag tgc    1874
Trp Trp Thr Gln Gln Ser Ala Ser Asn Phe Lys Glu Gln Ser Gln Cys
            610             615             620 atg gtg tat cag tat gga aac ttt tcc tgg gac ctg gca ggt gga cag    1922
Met Val Tyr Gln Tyr Gly Asn Phe Ser Trp Asp Leu Ala Gly Gly Gln
            625             630             635 cac ctt aat gga att aat aca ctg gga gaa aac att gct gat aat gga    1970
His Leu Asn Gly Ile Asn Thr Leu Gly Glu Asn Ile Ala Asp Asn Gly
            640             645             650 ggt ctt ggt caa gca tac aga gcc tat cag aat tat att aaa aag aat    2018
Gly Leu Gly Gln Ala Tyr Arg Ala Tyr Gln Asn Tyr Ile Lys Lys Asn
        655             660             665 ggc gaa gaa aaa tta ctt cct gga ctt gac cta aat cac aaa caa cta    2066
Gly Glu Glu Lys Leu Leu Pro Gly Leu Asp Leu Asn His Lys Gln Leu
670             675             680             685 ttt ttc ttg aac ttt gca cag gtg tgg tgt gga acc tat agg cca gag    2114
Phe Phe Leu Asn Phe Ala Gln Val Trp Cys Gly Thr Tyr Arg Pro Glu
            690             695             700 tat gcg gtt aac tcc att aaa aca gat gtg cac agt cca ggc aat ttc    2162
Tyr Ala Val Asn Ser Ile Lys Thr Asp Val His Ser Pro Gly Asn Phe
        705             710             715 agg att att ggg act ttg cag aac tct gca gag ttt tca gaa gcc ttt    2210
Arg Ile Ile Gly Thr Leu Gln Asn Ser Ala Glu Phe Ser Glu Ala Phe
        720             725             730 cac tgc cgc aag aat tca tac atg aat cca gaa aag aag tgc cgg gtt    2258
His Cys Arg Lys Asn Ser Tyr Met Asn Pro Glu Lys Lys Cys Arg Val
        735             740             745 tgg tga tcttcaaaag aagcattgca gcccttggct agacttgcca acaccacaga    2314
Trp
750 aatggggaat tctctaatcg aaagaaaatg ggccctaggg gtcactgtac tgacttgagg    2374 gtgattaaca gagagggcac catcacaata cagataacat taggttgtcc tagaaagggt    2434 gtggagggag gaaggggtc taaggtctat caagtcaatc atttctcact gtgtacataa    2494 tgcttaattt ctaaagataa tattactgtt tatttctgtt tctcatatgg tctaccagtt    2554 tgctgatgtc cctagaaaac aatgcaaaac ctttgaggta gaccaggatt tctaatcaaa    2614 agggaaaaga agatgttgaa gaatagagtt aggcaccaga agaagagtag gtgacactat    2674 agtttaaaac acattgccta actactagtt tttactttta tttgcaacat ttacagtcct    2734 tcaaaatcct tccaaagaat tcttatacac attgggcct tggagcttac atagttttaa    2794 actcattttt gccatacatc agttattcat tctgtgatca tttatttaa gcactcttaa    2854 agcaaaaaat gaatgtctaa aattgttttt tgttgtacct gctttgactg atgctgagat    2914 tcttcaggct tcctgcaatt ttctaagcaa tttcttgctc tatctctcaa aacttggtat    2974 ttttcagaga tttatataaa tgtaaaaata ataattttta tatttaatta ttaactacat    3034 ttatgagtaa ctattattat aggtaatcaa tgaatattga agtttcagct taaaataaac    3094 agttgtgaac caagatctat aaagcgatat acagatgaaa atttgagact atttaaactt    3154 ataaatcata ttgatgaaaa gatttaagca caaacttag ggtaaaaatt gcgattggac    3214
```

```
agttgtctag agatatatat acttgtggtt ttcaaattgg actttcaaaa ttaaatctgt   3274
ccctgagagt gtctctgata aagggcaaa tctgcaccta tgtagctctg catctcctgt    3334
cttttcaggt ttgtcatcag atggaaatat tttgataata aattgaaatt gtgaactcat   3394
tgctccctaa gactgtgaca actgtctaac tttagaagtg catttctgaa tagaaatggg   3454
aggcctctga tggaccttct agaattataa gtcacaaaga gttctggaaa agaactgttt   3514
actgcttgat aggaattcat cttttgaggc ttctgttcct ctcttttcct gttgtattga   3574
ctatttcgt tcattacttg attaagattt tacaaaagag gagcacttcc aaaattctta   3634
tttttcctaa caaaagatga agcagggaa tttctatcta aatgatgagt attagttccc    3694
tgtctcttga aaaatgccca tttgccttta aaaaaaaag ttacagaaat actataacat    3754
atgtacataa attgcataaa gcataagtat acagttcaat aaacttaact ttaactgaac   3814
aatggccctg tagccagcac ctgtaagaaa cagagcagta ccagcgctct aaaagcacct   3874
ccttgtcact ttattactcc cagaacaaca actatcctga cttctaatat cattcactag   3934
ctttgcctgg ttttgtcttt tatgcagata gaatcaatca gtatgtattc ttttgtgcct   3994
ggcttctttc tctcagcctt acatttgtga gattcctctg tattgtgctg attgtggatc   4054
ttttcattct cattgcagaa taatgttcta ttgtgggact tattacaatt tgttcatcct   4114
attgttgatg ggcacttgag aactttccat tttggcgcta ttacaaatag tgcaactatg   4174
aatgtactgc atgttaccat cttacttgag cctttaatgg acttatttct tcaaatcctt   4234
ccaaaaatta ttataagcat tgaaattata gtttcaagcc aactgtggat acccttaccc   4294
tttcctcctt tatcacaacc accgttacaa gtatacttat atttccctaa aatacattta   4354
aaacttacct aagtgacatt tgtagttgga gtaataggag cttccagctc taataaaaca   4414
gctgtctcta acttatttta tttccatcat gtcagagcag gtgaagagcc agaagtgaag   4474
agtgactagt acaaattata aaagccact agactcttca ctgttagctt tttaaaacat    4534
taggctccca tccctatgga ggaacaactc tccagtgcct ggatcccctc tgtctacaaa   4594
tataagattt tctgggccta aaggatagat caaagtcaaa aatagcaatg cctcccatc    4654
cctcacacat ccagacatca tgaattttac atggtactct tgttgagttc tatagagcct   4714
tctgatgtct ctaaagcact accgattctt tggagttgtc acatcagata agacatatct   4774
ctaattccat ccataaatcc agttctacta tggctgagtt ctggtcaaag aaagaaagtt   4834
tagaagctga gacacaaagg gttgggagct gatgaaactc acaaatgatg gtaggaagaa   4894
gctctcgaca atacccgttg gcaaggagtc tgcctccatg ctgcagtgtt cgagtggatt   4954
gtaggtgcaa gatggaaagg attgtaggtg caagctgtcc agagaaaaga gtccttgttc   5014
cagccctatt ctgccactcc tgacagggtg accttgggta tttgcaatat cctttgggc    5074
ctctgcttct ctcacctaaa aaagagaat tagattatat tggtggttct cagcaagaga    5134
aggagtatgt gtccaatgct gccttcccat gaatctgtct cccagttatg aatcagtggg   5194
caggataaac tgaaaactcc catttaagtg tctgaatcga gtgagacaaa attttagtcc   5254
aaataacaag taccaaagtt ttatcaagtt tgggtctgtg ctgctgttac tgttaaccat   5314
ttaagtgggg caaaaccttg ctaatttct caaaagcatt tatcattctt gttgccacag    5374
ctggagctct caaactaaaa gacatttgtt attttggaaa gagaaagac tctattctca    5434
aagtttccta atcagaaatt tttatcagtt tccagtctca aaaatacaaa ataaaaacaa   5494
acgtttttaa tact                                                    5508
```

<210> SEQ ID NO 4
<211> LENGTH: 750
<212> TYPE: PRT
<213> ORGANISM: Homo sapiens

<400> SEQUENCE: 4

```
Met Gly Lys Ser Glu Ser Gln Met Asp Ile Thr Asp Ile Asn Thr Pro
1               5                   10                  15
Lys Pro Lys Lys Lys Gln Arg Trp Thr Arg Leu Glu Ile Ser Leu Ser
            20                  25                  30
Val Leu Val Leu Leu Leu Thr Ile Ile Ala Val Arg Met Ile Ala Leu
        35                  40                  45
Tyr Ala Thr Tyr Asp Asp Gly Ile Cys Lys Ser Ser Asp Cys Ile Lys
    50                  55                  60
Ser Ala Ala Arg Leu Ile Gln Asn Met Asp Ala Thr Thr Glu Pro Cys
65                  70                  75                  80
Arg Asp Phe Phe Lys Tyr Ala Cys Gly Gly Trp Leu Lys Arg Asn Val
                85                  90                  95
Ile Pro Glu Thr Ser Ser Arg Tyr Gly Asn Phe Asp Ile Leu Arg Asp
            100                 105                 110
Glu Leu Glu Val Val Leu Lys Asp Val Leu Gln Glu Pro Lys Thr Glu
        115                 120                 125
Asp Ile Val Ala Val Gln Lys Ala Lys Ala Leu Tyr Arg Ser Cys Ile
    130                 135                 140
Asn Glu Ser Ala Ile Asp Ser Arg Gly Gly Glu Pro Leu Leu Lys Leu
145                 150                 155                 160
Leu Pro Asp Ile Tyr Gly Trp Pro Val Ala Thr Glu Asn Trp Glu Gln
                165                 170                 175
Lys Tyr Gly Ala Ser Trp Thr Ala Glu Lys Ala Ile Ala Gln Leu Asn
            180                 185                 190
Ser Lys Tyr Gly Lys Lys Val Leu Ile Asn Leu Phe Val Gly Thr Asp
        195                 200                 205
Asp Lys Asn Ser Val Asn His Val Ile His Ile Asp Gln Pro Arg Leu
    210                 215                 220
Gly Leu Pro Ser Arg Asp Tyr Tyr Glu Cys Thr Gly Ile Tyr Lys Glu
225                 230                 235                 240
Ala Cys Thr Ala Tyr Val Asp Phe Met Ile Ser Val Ala Arg Leu Ile
                245                 250                 255
Arg Gln Glu Glu Arg Leu Pro Ile Asp Glu Asn Gln Leu Ala Leu Glu
            260                 265                 270
Met Asn Lys Val Met Glu Leu Glu Lys Glu Ile Ala Asn Ala Thr Ala
        275                 280                 285
Lys Pro Glu Asp Arg Asn Asp Pro Met Leu Leu Tyr Asn Lys Met Arg
    290                 295                 300
Leu Ala Gln Ile Gln Asn Asn Phe Ser Leu Glu Ile Asn Gly Lys Pro
305                 310                 315                 320
Phe Ser Trp Leu Asn Phe Thr Asn Glu Ile Met Ser Thr Val Asn Ile
                325                 330                 335
Ser Ile Thr Asn Glu Glu Asp Val Val Val Tyr Ala Pro Glu Tyr Leu
            340                 345                 350
Thr Lys Leu Lys Pro Ile Leu Thr Lys Tyr Ser Ala Arg Asp Leu Gln
        355                 360                 365
Asn Leu Met Ser Trp Arg Phe Ile Met Asp Leu Val Ser Ser Leu Ser
    370                 375                 380
```

-continued

```
Arg Thr Tyr Lys Glu Ser Arg Asn Ala Phe Arg Lys Ala Leu Tyr Gly
385                 390                 395                 400

Thr Thr Ser Glu Thr Ala Thr Trp Arg Arg Cys Ala Asn Tyr Val Asn
            405                 410                 415

Gly Asn Met Glu Asn Ala Val Gly Arg Leu Tyr Val Glu Ala Ala Phe
            420                 425                 430

Ala Gly Glu Ser Lys His Val Val Glu Asp Leu Ile Ala Gln Ile Arg
            435                 440                 445

Glu Val Phe Ile Gln Thr Leu Asp Asp Leu Thr Trp Met Asp Ala Glu
    450                 455                 460

Thr Lys Lys Arg Ala Glu Glu Lys Ala Leu Ala Ile Lys Glu Arg Ile
465                 470                 475                 480

Gly Tyr Pro Asp Asp Ile Val Ser Asn Asp Asn Lys Leu Asn Asn Glu
            485                 490                 495

Tyr Leu Glu Leu Asn Tyr Lys Gly Asp Glu Tyr Phe Glu Asn Ile Ile
            500                 505                 510

Gln Asn Leu Lys Phe Ser Gln Ser Lys Gln Leu Lys Lys Leu Arg Glu
    515                 520                 525

Lys Val Asp Lys Asp Glu Trp Ile Ser Gly Ala Ala Val Val Asn Ala
    530                 535                 540

Phe Tyr Ser Ser Gly Arg Asn Gln Ile Val Phe Pro Ala Gly Ile Leu
545                 550                 555                 560

Gln Pro Pro Phe Phe Ser Ala Gln Gln Ser Asn Ser Leu Asn Tyr Gly
            565                 570                 575

Gly Ile Gly Met Val Ile Gly His Glu Ile Thr His Gly Phe Asp Asp
            580                 585                 590

Asn Gly Arg Asn Phe Asn Lys Asp Gly Asp Leu Val Asp Trp Trp Thr
            595                 600                 605

Gln Gln Ser Ala Ser Asn Phe Lys Glu Gln Ser Gln Cys Met Val Tyr
    610                 615                 620

Gln Tyr Gly Asn Phe Ser Trp Asp Leu Ala Gly Gly Gln His Leu Asn
625                 630                 635                 640

Gly Ile Asn Thr Leu Gly Glu Asn Ile Ala Asp Asn Gly Gly Leu Gly
            645                 650                 655

Gln Ala Tyr Arg Ala Tyr Gln Asn Tyr Ile Lys Lys Asn Gly Glu Glu
            660                 665                 670

Lys Leu Leu Pro Gly Leu Asp Leu Asn His Lys Gln Leu Phe Phe Leu
    675                 680                 685

Asn Phe Ala Gln Val Trp Cys Gly Thr Tyr Arg Pro Glu Tyr Ala Val
    690                 695                 700

Asn Ser Ile Lys Thr Asp Val His Ser Pro Gly Asn Phe Arg Ile Ile
705                 710                 715                 720

Gly Thr Leu Gln Asn Ser Ala Glu Phe Ser Glu Ala Phe His Cys Arg
            725                 730                 735

Lys Asn Ser Tyr Met Asn Pro Glu Lys Lys Cys Arg Val Trp
            740                 745                 750
```